(12) United States Patent
Freeman et al.

(10) Patent No.: US 10,030,270 B2
(45) Date of Patent: Jul. 24, 2018

(54) K-RAS MUTATIONS AND ANTI-EGFR ANTIBODY THERAPY

(75) Inventors: Daniel Freeman, Newbury Park, CA (US); Todd Juan, Newbury Park, CA (US); Robert Radinsky, Thousand Oaks, CA (US)

(73) Assignee: AMGEN, INC, Thousand Oaks, CA (US)

( * ) Notice: Subject to any disclaimer, the term of this patent is extended or adjusted under 35 U.S.C. 154(b) by 0 days.

(21) Appl. No.: 13/523,174

(22) Filed: Jun. 14, 2012

(65) Prior Publication Data

US 2012/0264129 A1    Oct. 18, 2012

Related U.S. Application Data

(63) Continuation of application No. 12/046,319, filed on Mar. 11, 2008.

(60) Provisional application No. 60/906,943, filed on Mar. 13, 2007.

(51) Int. Cl.
*A61K 39/00* (2006.01)
*C12Q 1/6886* (2018.01)

(52) U.S. Cl.
CPC ...... *C12Q 1/6886* (2013.01); *C12Q 2600/118* (2013.01)

(58) Field of Classification Search
None
See application file for complete search history.

(56) References Cited

U.S. PATENT DOCUMENTS

| | | | |
|---|---|---|---|
| 6,503,914 B1 | 1/2003 | Benish et al. | |
| 7,294,468 B2 | 11/2007 | Bell et al. | |
| 7,932,026 B2 | 4/2011 | Seshagiri | |
| 8,293,501 B2 * | 10/2012 | Fredriksson | C12Q 1/686 435/91.2 |
| 2005/0272083 A1 * | 12/2005 | Seshagiri | 435/6 |
| 2006/0141497 A1 * | 6/2006 | Finkelstein | C12Q 1/6806 435/6.14 |
| 2007/0254295 A1 | 11/2007 | Harvey et al. | |
| 2009/0075267 A1 | 3/2009 | Siena et al. | |
| 2009/0202989 A1 | 8/2009 | Hillan | |
| 2010/0221754 A1 * | 9/2010 | Ford et al. | 435/7.23 |

FOREIGN PATENT DOCUMENTS

| | | |
|---|---|---|
| WO | WO 2004/111273 A2 | 12/2004 |
| WO | WO2007025044 * | 8/2005 |
| WO | 2005/118876 | 12/2005 |
| WO | WO 2006/107854 A2 | 10/2006 |
| WO | WO 2006/108627 A1 | 10/2006 |
| WO | 2007/011702 | 1/2007 |
| WO | WO 2007/001868 A1 | 1/2007 |
| WO | WO 2007/025044 A2 | 3/2007 |
| WO | WO2007025044 * | 3/2007 |

OTHER PUBLICATIONS

Lievre et al, Cancer Res. vol. 3992-5, Apr. 2006.*
Pao et al PLoS Medicine 2:57-61, Jan. 2005.*
Commu oncology, 3:3-16, Oct. 2006.*
CenterWatch.com pub, 2006.*
Malik et al, J clin Onco ASCO meeting abstract, vol. 23 #3520, Jun. 2005.*
BucFord et al (BioTechniques 27:528-536, 1999).*
U.S. Appl. No. 60/695,174, filed Jun. 28, 2005, Hillan.
U.S. Appl. No. 60/711,054, filed Aug. 24, 2005, Ford et al.
Allison, "Is personalized medicine finally arriving?" *Nat. Biotech.*, 26: 509-517 (2008).
Amado et al., "Analysis of KRAS mutations in patients with metastatic colorectal cancer receiving panitumumab monotherapy," *Eur. J. of Cancer Suppl.*, 5: 8 (2007).
Amado et al, "Panitumumab (pmab) efficacy and patient-reported outcomes (PRO) in metastatic colorectal cancer (mCRC) patients (pts) with wild-type (WT) *KRAS* tumor status," *ASCO*, Abstract No: 278 (2008).
Amado et al., "Wild-type KRAS is required for panitumumab efficacy in patients with metastatic colorectal cancer," *J. Clin. Oncol.*, 26:1626-1634 (2008).
Amgen press release, "New biomarker data links KRAS gene to Vectibix™ clinical response," Sep. 25, 2007. http://www.amgen.com/media/media_pr_detail.jsp?year=2007&releaseID=1055062.
Amler et al., "Predicting clinical benefit in non-small-cell lung cancer patients treated with epidermal growth factor tyrosine kinase inhibitors," *Cold Spring Harbor Symp. Quant.Biol.*, 70: 483-488 (2005).
Andreyev et al., "Kirsten ras mutations in patients with colorectal cancer: the 'RASCAL II' study," *Br. J. of Canc.*, 85: 692-696 (2001).
Bardelli, "Terapie personalizzate per it tumore del colon con analisi genomiche scoperte a Candiolo e a Niguarda," *OCGO*, 4(1): 4-5 (2007), with English translation.
Baselga et al., "Determinants of RASistance to anti—epidermal growth factor receptor agents," *J. Clin. Oncol.*, 26: 1582-1584 (2008).
Bazan et al., "Specific codon 13 K-ras mutations are predictive of clinical outcome in colorectal cancer patients, whereas codon 12 K-ras mutations are associated with mucinous histotype," *Ann. Oncol.*, 13: 1438-1446 (2002).
Benvenuti et al., "Oncogenic activation of the RAS/RAF signaling pathway impairs the response of metastatic colorectal cancers to anti-epidermal growth factor receptor antibody therapies," *Cancer Res.*, 67: 2643-2648 (2007).
Bos et al., "Prevalence of ras gene mutations in human colorectal cancers," *Nature*, 327:293-297 (1987).
De Roock et al., "KRAS wild-type state predicts survival and is associated to early radiological response in metastatic colorectal cancer treated with cetuximab," *Ann. Oncol.*, 19: 508-515 (2008), published online Nov. 12, 2007.
Di Fiore et al., "Clinical relevance of KRAS mutation detection in metastatic colorectal cancer treated by Cetuximab plus chemotherapy," *Br. J. Cancer*, 96:1166-1169 (2007).

(Continued)

*Primary Examiner* — Lei Yao
(74) *Attorney, Agent, or Firm* — Cynthia T. Chen

(57) ABSTRACT

The present application relates to K-ras mutations, to polynucleotides encoding mutant K-ras polypeptides, and to methods of identifying K-ras mutations. The present application also relates to methods of diagnosing cancer; and methods and kits for predicting the usefulness of anti-EGFr specific binding agents in the treatment of tumors.

3 Claims, 9 Drawing Sheets

(56) References Cited

OTHER PUBLICATIONS

Eberhard et al., "Correlation of mutations in EGFR with clinical outcomes in NSCLC patients treated with erlotinib," *EJC Supplements*, Proceedings of the 16th EORTC-NCI-AACR *Symposium on Molecular Targets and Cancer Therapeutics*, 2: 124 (2004).
Eberhard et al, "Mutations in the Epidermal Growth Factor Receptor and in KRAS are predictive and prognostic indicators in patients with non-small-cell lung cancer treated with chemotherapy alone and in combination with erlotinib," *J. Clin. Oncol.*, 23: 5900-5909 (2005).
Editorial, "Looking forward, looking back," *Nat. Biotech.*, 26: 475 (2008).
Esteller et al., "K-ras and p16 aberrations confer poor prognosis in human colorectal cancer," *J. Clin. Oncol.*, 19: 299-304 (2001).
Finocchiaro et al., "EGFR, HER2 and Kras as predictive factors for cetuximab sensitivity in colorectal cancer," *ASCO*, Abstract No. 4021 (2007).
Forrester et al., "Detection of high incidence of K-ras oncogenes during human colon tumorigenesis," *Nature*, 327:298-303 (1987).
Fransén et al., "Mutation analysis of the BRAF, ARAF and RAF-1 genes in human colorectal adenocarcinomas," *Carcinogenesis*, 25: 527-533 (2004).
Freeman et al., "Association of somatic KRAS gene mutations and clinical outcome in patients (pts) with metastatic colorectal cancer (mCRC) receiving panitumumab monotherapy," *ECCO* 14, Abstract O#3014 (2007).
Hecht et al, "Interim results from PACCE: Irinotecan (Iri)/bevacizumab (bev) ± panitumumab (pmab) as first-line treatment (tx) for metastatic colorectal cancer (mCRC)," *ASCO*, Absract No: 279 (2008).
Hecht et al., "Panitumumab (pmab) efficacy in patients (pts) with metastatic colorectal cancer (mCRC) with low or undetectable levels of epidermal growth factor receptor (EGFr): Final efficacy and KRAS analyses," *ASCO*, Abtract No: 343 (2008).
Ince et al., "Association of k-ras, b-raf, and p53 Status with the treatment effect of bevacizumab," *J. Natl. Cancer Inst.*, 97: 981-989 (2005).
Juan et al., "A comparability study of 4 commercial KRAS tests," *AACR*, Abstract (2008).
Khambata-Ford et al., "Expression of epiregulin and amphiregulin and K-ras mutation status predict disease control in metastatic colorectal cancer patients treated with cetuximab," *J. Clin. Oncol.*, 25: 3230-3237 (2007).
Lièvre et al., "KRAS mutation status is predictive of response to cetuximab therapy in colorectal cancer," *Cancer Res.*, 66: 3992-3995 (2006).
Lièvre et al., "KRAS mutations in colorectal cancer is a predictive factor of response and progression free survival in patients treated with Cetuximab," Abstract 5671, AACR Proceedings (2007).
Lièvre et al., "KRAS mutations as an independent prognostic factor in patients with advanced colorectal cancer treated with cetuximab," *J. Clin. Oncol.*, 26: 374-379 (2008).
Malumbres et al., "RAS oncogenes: the first 30 years," *Nat. Rev.*, 3: 7-13 (2003).
Moroni et al., "Gene copy of number for epidermal growth factor receptor (EGFR) and clinical response to antiEGFR treatment in colorectal cancer: a cohort study," *Lancet Oncol.*, 6: 279-286 (2005).
Moroni et al. "Somatic mutation of EGFR catalytic domain and treatment with gefitinib in colorectal cancer," *Ann. Onc.*, 16: 1848-1849 (2005).
Moroni et al., "EGFR Fish in colorectal cancer: what is the current reality?" *Lancet Oncol.*, 9: 402-403 (2008).
Pao et al., "*KRAS* mutations and primary resistance of lung adenocarcinomas to gefitinib or erlotinib," *PLoS Medicine*, 2:57-61 (2005).
Porges et al., "DNA, AMGN, Merck KGaA: Could KRAS save Vectibix? Could it impact Avastin? Chasing the genomic breakthrough," *Bernstein Research*, Oct. 8, 2007.
Santos et al, "Malignant activation of a K-ras oncogene in lung carcinoma but not in normal tissue of the same patient," *Science*, 223: 661-664 (1984).
Sartore-Bianchi et al., "Anti-EGFR monoclonal antibodies in the treatment of non-small cell lung cancer," *Ann. Onc.*, 17(suppl. 2): ii49-ii51 (2006).
Sartore-Bianchi et al., "Epidermal growth factor receptor gene copy number and clinical outcome of metastatic colorectal cancer treated with panitumumab," *J. Clin. Oncol.*, 25: 3238-3245 (2007).
Van Custsem et al., "Open-Label phase III trial of panitumumab plus best supportive care compared with best supportive care alone in patients with chemotherapy-refractory metastatic colorectal cancer," *J. Clin. Oncol.*, 25: 1658-1664 (2007).
Vogelstein et al., "Genetic alterations during colorectal-tumor development," *N. Engl. J. Med.*, 319:525-532 (1998).
Products—KRAS status predicts non-response to Amgen's Vectibix in metastatic colorectal cancer, www.scripnews.com, 3300: 18-19 (2007).
Transformative discoveries—A timeline of KRAS Research, Amgen Oncology (2007).
Caraglia et al., "EGF-R small inhibitors and anti-EGF-R antibodies: advantages and limits of a new avenue in anticancer therapy," *Recent Patents on Anti-Cancer Drug Discovery*, 1:209-222 (2006).
Chua et al., "Panitumumab," *Drugs of Today*, 42:711-719 (2006).
Friday et al., "K-ras as a target for cancer therapy," *Biochimica et Biophysica Acta*, 1756:127-144 (2005).
PCT Invitation to Pay Additional Fees and Annex to Form PCT/ISA/206, Communication Relating to the Results of the Partial International Search, received in PCT International Application No. PCT/US2008/003327, faxed Sep. 11, 2008.
PCT Notification of Transmittal of the International Search Report and the Written Opinion of the International Searching Authority for International Application No. PCT/US2008/003312, dated Sep. 30, 2008.
PCT Notification of Transmittal of the International Search Report and the Written Opinion of the International Searching Authority, or the Declaration, for International Application No. PCT/US2008/003327, dated Oct. 31, 2008.
Eberhard et al., "Mutations in EGFR, HER2, KRAS, and BRAF in NSCLC: Prevalences and correlations with clinical outcomes in patients treated with carboplatin and paclitaxel with or without erlotinib," Abstract No. O-186, *Lung Cancer*, 49: S62 (2005).
Braun et al., "Somatic activation of oncogenic Kras in hematopoietic cells initiates a rapidly fatal myeloproliferative disorder," *Proc. Natl. Acad. Sci., U.S.A.*, 101(2): 597-602 (2004).
Communication pursuant to Article 94(3) EPC for European Patent App. No. 08742064.2, dated Dec. 30, 2009 (3 pages).
Letter in response to the Communication under Rules 161/162 EPC dated Oct. 20, 2009, for European Patent App. No. 08742064.2, dated Nov. 23, 2009 (11 pages).
Communication pursuant to Rules 161 and 162 EPC dated Oct. 20, 2009, for European Patent App. No. 08742064.2 (2 pages).
Communication pursuant to Article 94(3) EPC for European Patent App. No. 08742061.8, dated Jan. 27, 2010 (4 pages).
Communication pursuant to Rules 161 and 162 EPC dated Oct. 20, 2009, for European Patent App. No. 08742061.8 (2 pages).
Restriction Requirement dated Sep. 24, 2009, for U.S. Appl. No. 12/046,312 (7 pages).
Response to Restriction Requirement, filed Nov. 24, 2009, for U.S. Appl. No. 12/046,312 (3 pages).
Non-final Office Action dated Feb. 1, 2010, for U.S. Appl. No. 12/046,312 (16 pages).
W. Brugger et al., "Prospective Molecular Marker Analyses of EGFR and KRAS From a Randomized, Placebo-Controlled Study of Erlotinib Maintenance Therapy in Advanced Non-Small-Cell Lung Cancer," *J. Clin. Oncol.*, 29, published online Oct. 3, 2011 (10 pages).
S. Khambata-Ford et al., "Analysis of Potential Predictive Markers of Cetuximab Benefit in BMS099, a Phase III Study of Cetuximab

(56) References Cited

OTHER PUBLICATIONS and First-Line Taxane/Carboplatin in Advanced Non-Small-Cell Lung Cancer," *J. Clin. Oncol.*, 28(6): 918-927 (2010).
C. Langer, "Roles of EGFR and KRAS Mutations in the Treatment of Patients With Non-Small-Cell Lung Cancer," *Pharmacy & Therapeutics*, 36(5): 263-268 and 277-279 (2011).
K. O'Byrne et al., "Molecular biomarkers in non-small-cell lung cancer: a retrospective analysis of data from the phase 3 FLEX study," *Lancet Oncol.*, 12: 795-805 (2011).
P. Roberts et al., "Personalized Medicine in Non-Small-Cell Lung Cancer: Is KRAS a Useful Marker in Selecting Patients for Epidermal Growth Factor Receptor-Targeted Therapy?," *J. Clin. Oncol.*, 28(31): 4769-4777 (2010).
Amgen Inc., "Background Information for the Oncologic Drugs Advisory Committee (ODAC) Meeting Dec. 16, 2008," published by Amgen Inc., Thousand Oaks, CA (59 pages).
Certified U.S. Appl. No. 60/711,054, filed Aug. 24, 2005, related to PCT App. No. PCT/US06/33073 (46 pages).
Notice of Abandonment, dated Apr. 19, 2011, for U.S. Appl. No. 12/046,312 (2 pages).
Final Office Action, dated Aug. 4, 2010, for U.S. Appl. No. 12/046,312 (11 pages).
Reply to Office Action, dated Jun. 3, 2010, for U.S. Appl. No. 12/046,312 (14 pages).
Letter in response to the Official Communication dated Dec. 30, 2009, for European Patent App. No. 08 742 064.2, filed Jul. 9, 2010 (13 pages).
Communication pursuant to Article 94(3) EPC, for European Patent App. No. 08 742 064.2, dated Mar. 29, 2011 (5 pages).
Letter in response to the Official Communication dated Jan. 27, 2010, for European Patent App. No. 08 742 061.8, filed Jul. 9, 2010 (9 pages).
W. De Roock et al., "Effects of KRAS, BRAF, NRAS, and PIK3CA mutations on the efficacy of cetuximab plus chemotherapy in chemotherapy-refractory metastatic colorectal cancer: a retrospective consortium analysis," *Lancet Oncol.*, 11: 753-762 (2010).
F. Di Nicolantonio et al., "Wild-Type BRAF Is Required for Response to Panitumumab or Cetuximab in Metastatic Colorectal Cancer," *J. Clin. Oncol.*, 26(35): 5705-5712 (2008).
P. Laurent-Puig et al., "Analysis of PTEN, BRAF, and EGFR Status in Determining Benefit From Cetuximab Therapy in Wild-Type KRAS Metastatic Colon Cancer," *J. Clin. Oncol.*, 27(35): 5924-5930 (2009).
C. Mao et al., "BRAF V600E mutation and resistance to anti-EGFR monoclonal antibodies in patients with metastatic colorectal cancer: a meta-analysis," *Mol. Biol. Rep.*, 38: 2219-2223 (2011).
W.S. Samowitz et al., "Poor Survival Associated with the BRAF V600E Mutation in Microsatellite-Stable Colon Cancers," *Cancer Res.*, 65(14): 6063-6069 (2005).
Extended European Search Report for European Patent Application No. 11184356.1, dated Jan. 2, 2012 (9 pages).
Notice of Third Party Observation, dated Feb. 9, 2012, for Japanese Patent Application No. 2009-553625 (48 pages).
Notice of Third Party Observation, dated Feb. 9, 2012, for Japanese Patent Application No. 2009-553623 (18 pages).
C. J. Farr et al., "Analysis of RAS gene mutations in acute myeloid leukemia by polymerase chain reaction and oligonucleotide probes," *Proc. Natl. Acad. Sci. USA*, 85: 1629-1633 (1988).
S. Ogino et al., "Molecular Alterations in Tumors and Response to Combination Chemotherapy with Getfitinib for Advanced Colorectal Cancer," *Clin. Cancer Res.*, 11: 6650-6656 (2005).
E. Grothey, "New treatment options for patients with metastatic colorectal cancer," *Community Oncol*, 3(10, Supp. 4): 3-9 (2006).
M. Raponi et al., "KRAS mutations predict response to EGFR inhibitors," *Curr. Opin. Pharmacol.*, 8: 413-418 (2008).
S. Edkins et al., "Recurrent KRAS Codon 146 Mutations in Human Colorectal Cancer," *Cancer Biol. & Therapy*, 5(8): 928-932 (2006).
K. Kato et al., "Oncogenic Ras Modulates Epidermal Growth Factor Responsiveness in Endometrial Carcinomas," *Eur. J. Cancer*, 34(5): 737-744 (1998).
Restriction Requirement, dated Aug. 13, 2009, for U.S. Appl. No. 12/046,319 (7 pages).
Response, filed Sep. 14, 2009, for U.S. Appl. No. 12/046,319 (4 pages).
Non-final Office Action, dated Nov. 23, 2009, for U.S. Appl. No. 12/046,319 (15 pages).
Reply to Office Action, filed May 24, 2010, for U.S. Appl. No. 12/046,319 (7 pages).
Final Office Action, dated Aug. 6, 2010, for U.S. Appl. No. 12/046,319 (13 pages).
Amendment and Response to Prior Office Action, filed Dec. 21, 2010, for U.S. Appl. No. 12/046,319 (5 pages).
Non-final Office Action, dated Apr. 13, 2011, for U.S. Appl. No. 12/046,319 (10 pages).
Reply to Office Action, filed Oct. 13, 2011, for U.S. Appl. No. 12/046,319 (10 pages).
Final Office Action, dated Dec. 15, 2011, for U.S. Appl. No. 12/046,319 (16 pages).
Reply to Final Office Action, filed Mar. 19, 2012, for U.S. Appl. No. 12/046,319 (15 pages).
Advisory Action, dated Apr. 2, 2012, for U.S. Appl. No. 12/046,319 (4 pages).
Restriction Requirement, dated Dec. 8, 2011, for U.S. Appl. No. 12/976,895 (5 pages).
Response to Restriction Requirement, filed Apr. 23, 2012, for U.S. Appl. No. 12/976,895 (2 pages).
Augello et al. "TP53 and p16INK4A, but not H-KI-Ras, are Involved in Tumorigenesis and Progression of Pleomorphic Adenomas", J of Cellular Physiology, V 207, No. 3, 654-659, Jun. 2006.
Caraglia, et al. "EGF-R Small Inhibitors and Anti-EGF-R Antibodies: Advantages and Limits of a New Avenue in Anticancer Therapy", Recent Patents on Anticancer Drug Discovery, V 1, No. 2, 209-222, Jun. 2006.
Garassino et al. "Effect of tumor-specific KRAS mutational status on impact of anti-EGFR therapy in non-small cell lung cancer", Journal of Clinical Oncology, 28(15s) abstract 7564, 2010.
Kirk, Rebecca, "Genetics: In colorectal cancer, not all KRAS mutations are created equal", Nature Reviews. Clinical Oncology, Jan. 2011, p. 1.
Mukohara et al., "Differential Effects of Gefitinib and Cetuximab on Non-small-cell Lung Cancers Bearing Epidermal Growth Factor Receptor Mutations" *J. Natl. Cancer Inst.*, 97: 1185-1194 (2005).

\* cited by examiner

FIGURE 1A (SEQ ID NO: 1)  Wild-type K-ras cDNA

ATGACTGAAT ATAAACTTGT GGTAGTTGGA GCTGGTGGCG TAGGCAAGAG TGCCTTGACG ATACAGCTAA  70
TTCAGAATCA TTTTGTGGAC GAATATGATC CAACAATAGA GGATTCCTAC AGGAAGCAAG TAGTAATTGA 140
TGGAGAAACC TGTCTCTTGG ATATTCTCGA CACAGCAGGT CAAGAGGAGT ACAGTGCAAT GAGGGACCAG 210
TACATGAGGA CTGGGGAGGG CTTTCTTTGT GTATTTGCCA TAAATAATAC TAAATCATTT GAAGATATTC 280
ACCATTATAG AGAACAAATT AAAAGAGTTA AGGACTCTGA AGATGTACCT ATGGTCCTAG TAGGAAATAA 350
ATGTGATTTG CCTTCTAGAA CAGTAGACAC AAAACAGGCT CAGGACTTAG CAAGAAGTTA TGGAATTCCT 420
TTTATTGAAA CATCAGCAAA GACAAGACAG GGTGTTGATG ATGCCTTCTA TACATTAGTT CGAGAAATTC 490
GAAAACATAA AGAAAAGATG AGCAAAGATG GTAAAAAGAA GAAAAAGAAG TCAAAGACAA AGTGTGTAAT 560
TATGTAA 567

(SEQ ID NO: 2)  Wild-type K-ras amino acid sequence

MTEYKLVVVG AGGVGKSALT IQLIQNHFVD EYDPTIEDSY RKQVVIDGET  50
CLLDILDTAG QEEYSAMRDQ YMRTGEGFLC VFAINNTKSF EDIHHYREQI 100
KRVKDSEDVP MVLVGNKCDL PSRTVDTKQA QDLARSYGIP FIETSAKTRQ 150
GVDDAFYTLV REIRKHKEKM SKDGKKKKKK SKTKCVIM 188

FIGURE 1B (SEQ ID NO: 3) K-ras (G12S) cDNA

ATGACTGAAT ATAAACTTGT GGTAGTTGGA GCTAGTGGCG TAGGCAAGAG TGCCTTGACG ATACAGCTAA 70
TTCAGAATCA TTTGTGTGGAC GAATATGATC CAACAATAGA GGATTCCTAC AGGAAGCAAG TAGTAATTGA 140
TGGAGAAACC TGTCTCTTGG ATATTCTCGA CACAGCAGGT CAAGAGGAGT ACAGTGCAAT GAGGGACCAG 210
TACATGAGGA CTGGGGAGGG CTTTCTTTGT GTATTGCCA TAAATAATAC TAAATCATTT GAAGATATTC 280
ACCATTATAG AGAACAAATT AAAAGAGTTA AGGACTCTGA AGATGTACCT ATGGTCCTAG TAGGAAATAA 350
ATGTGATTTG CCTTCTAGAA CAGTAGACAC AAAACAGGCT CAGGACTTAG CAAGAAGTTA TGGAATTCCT 420
TTTATTGAAA CATCAGCAAA GACAAGACAG GGTGTTGATG ATGCCTTCTA TACATTAGTT CGAGAAATTC 490
GAAAACATAA AGAAAAGATG AGCAAAGATG GTAAAAAGAA GAAAAAAGAA TCAAAGACAA AGTGTGTAAT 560
TATGTAA 567

(SEQ ID NO: 4) K-ras (G12S) amino acid sequence

MTEYKLVVVG ASGVGKSALT IQLIQNHFVD EYDPTIEDSY RKQVVIDGET 50
CLLDILDTAG QEEYSAMRDQ YMRTGEGFLC VFAINNTKSF EDIHHYREQI 100
KRVKDSEDVP MVLVGNKCDL PSRTVDTKQA QDLARSYGIP FIETSAKTRQ 150
GVDDAFYTLV REIRKHKEKM SKDGKKKKKK SKTKCVIM 188

FIGURE 1C (SEQ ID NO: 5) K-ras (G12V) cDNA

ATGACTGAAT ATAAACTTGT GGTAGTTGGA GCTGTTGGCG TAGGCAAGAG TGCCTTGACG ATACAGCTAA 70
TTCAGAATCA TTTTGTGGAC GAATATGATC CAACAATAGA GGATTCCTAC AGGAAGCAAG TAGTAATTGA 140
TGGAGAAACC TGTCTCTTGG ATATTCTCGA CACAGCAGGT CAAGAGGAGT ACAGTGCAAT GAGGGACCAG 210
TACATGAGGA CTGGGGAGGG CTTTCTTTGT GTATTGCCA TAAATAATAC TAAATCATTT GAAGATATTC 280
ACCATTATAG AGAACAAATT AAAGAGTTA AGGACTCTGA AGATGTACCT ATGGTCCTAG TAGGAAATAA 350
ATGTGATTTG CCTTCTAGAA CAGTAGACAC AAAACAGGCT CAGGACTTAG CAAGAAGTTA TGGAATTCCT 420
TTTATTGAAA CATCAGCAAA GACAAGACAG GGTGTTGATG ATGCCTTCTA TACATTAGTT CGAGAAATTC 490
GAAAACATAA AGAAAAGATG AGCAAAGATG GTAAAAAGAA GAAAAAGAAG TCAAAGACAA AGTGTGTAAT 560
TATGTAA 567

(SEQ ID NO: 6) K-ras (G12V) amino acid sequence

MTEYKLVVVG AVGVGKSALT IQLIQNHFVD EYDPTIEDSY RKQVVIDGET 50
CLLDILDTAG QEEYSAMRDQ YMRTGEGFLC VFAINNTKSF EDIHHYREQI 100
KRVKDSEDVP MVLVGNKCDL PSRTVDTKQA QDLARSYGIP FIETSAKTRQ 150
GVDDAFYTLV REIRKHKEKM SKDGKKKKKK SKTKCVIM 188

FIGURE 1D (SEQ ID NO: 7) K-ras (G12D) cDNA

ATGACTGAAT ATAAACTTGT GGTAGTTGGA GCTGATGGCG TAGGCAAGAG TGCCTTGACG ATACAGCTAA 70
TTCAGAATCA TTTTGTGGAC GAATATGATC CAACAATAGA GGATTCCTAC AGGAAGCAAG TAGTAATTGA 140
TGGAGAAACC TGTCTCTTGG ATATTCTCGA CACAGCAGGT CAAGAGGAGT ACAGTGCAAT GAGGGACCAG 210
TACATGAGGA CTGGGGAGGG CTTTCTTTGT GTATTGCCA CTAAATAATAC TAAATCATTT GAAGATATTC 280
ACCATTATAG AGAACAAATT AAAAGAGTTA AGGACTCTGA AGATGTACCT ATGGTCCTAG TAGGAAATAA 350
ATGTGATTTG CCTTCTAGAA CAGTAGACAC AAAACAGGCT CAGGACTTAG CAAGAAGTTA TGGAATTCCT 420
TTTATTGAAA CATCAGCAAA GACAAGACAG GGTGTTGATG ATGCCTTCTA TACATTAGTT CGAGAAATTC 490
GAAAACATAA AGAAAAGATG AGCAAAGATG GTAAAAAGAA GAAAAAGAAG TCAAAGACAA AGTGTGTAAT 560
TATGTAA 567

(SEQ ID NO: 8) K-ras (G12D) amino acid sequence

MTEYKLVVVG ADGVGKSALT IQLIQNHFVD EYDPTIEDSY RKQVVIDGET 50
CLLDILDTAG QEEYSAMRDQ YMRTGEGFLC VFAINNTKSF EDIHHYREQI 100
KRVKDSEDVP MVLVGNKCDL PSRTVDTKQA QDLARSYGIP FIETSAKTRQ 150
GVDDAFYTLV REIRKHKEKM SKDGKKKKKK SKTKCVIM 188

FIGURE 1E (SEQ ID NO: 9) K-ras (G12A) cDNA

```
ATGACTGAAT ATAAACTTGT GGTAGTTGGA GCTGCTGGCG TAGGCAAGAG TGCCTTGACG ATACAGCTAA  70
TTCAGAATCA TTTTGTGGAC GAATATGATC CAACAATAGA GGATTCCTAC AGGAAGCAAG TAGTAATTGA 140
TGGAGAAACC TGTCTCTTGG ATATTCTCGA CACAGCAGGT CAAGAGGAGT ACAGTGCAAT GAGGGACCAG 210
TACATGAGGA CTGGGGAGGG CTTTCTTTGT GTATTTGCCA TAAATAATAC TAAATCATTT GAAGATATTC 280
ACCATTATAG AGAACAAATT AAAAGAGTTA AGGACTCTGA AGATGTACCT ATGGTCCTAG TAGGAAATAA 350
ATGTGATTTG CCTTCTAGAA CAGTAGACAC AAAACAGGCT CAGGACTTAG CAAGAAGTTA TGGAATTCCT 420
TTTATTGAAA CATCAGCAAA GACAAGACAG GGTGTTGATG ATGCCTTCTA TACATTAGTT CGAGAAATTC 490
GAAAACATAA AGAAAAGATG AGCAAAGATG GTAAAAAGAA GAAAAAGAAG TCAAAGACAA AGTGTGTAAT 560
TATGTAA 567
```

(SEQ ID NO: 10) K-ras (G12A) amino acid sequence

```
MTEYKLVVVG AAGVGKSALT IQLIQNHFVD EYDPTIEDSY RKQVVIDGET  50
CLLDILDTAG QEEYSAMRDQ YMRTGEGFLC VFAINNTKSF EDIHHYREQI 100
KRVKDSEDVP MVLVGNKCDL PSRTVDTKQA QDLARSYGIP FIETSAKTRQ 150
GVDDAFYTLV REIRKHKEKM SKDGKKKKKK SKTKCVIM 188
```

FIGURE 1F (SEQ ID NO: 11) K-ras (G12C) cDNA

```
ATGACTGAAT ATAAACTTGT GGTAGTTGGA GCTTGTGGCG TAGGCAAGAG TGCCTTGACG ATACAGCTAA   70
TTCAGAATCA TTTTGTGGAC GAATATGATC CAACAATAGA GGATTCCTAC AGGAAGCAAG TAGTAATTGA  140
TGGAGAAACC TGTCTCTTGG ATATTCTCGA CACAGCAGGT CAAGAGGAGT ACAGTGCAAT GAGGACCAG   210
TACATGAGGA CTGGGGAGGG CTTTCTTTGT GTATTTGCCA TAAATAATAC TAAATCATTT GAAGATATTC  280
ACCATTATAG AGAACAAATT AAAAGAGTTA AGGACTCTGA AGATGTACCT ATGGTCCTAG TAGGAAATAA  350
ATGTGATTTG CCTTCTAGAA CAGTAGACAC AAAACAGGCT CAGGACTTAG CAAGAAGTTA TGGAATTCCT  420
TTTATTGAAA CATCAGCAAA GACAAGACAG GGTGTTGATG ATGCCTTCTA TACATTAGTT CGAGAAATTC  490
GAAAACATAA AGAAAAGATG AGCAAAGATG GTAAAAAGAA GAAAAAGAAG TCAAAGACAA AGTGTGTAAT  560
TATGTAA    567
```

(SEQ ID NO: 12) K-ras (G12C) amino acid sequence

```
MTEYKLVVVG ACGVGKSALT IQLIQNHFVD EYDPTIEDSY RKQVVIDGET   50
CLLDILDTAG QEEYSAMRDQ YMRTGEGFLC VFAINNTKSF EDIHHYREQI  100
KRVKDSEDVP MVLVGNKCDL PSRTVDTKQA QDLARSYGIP FIETSAKTRQ  150
GVDDAFYTLV REIRKHKEKM SKDGKKKKKK SKTKCVIM   188
```

FIGURE 1G (SEQ ID NO: 13) K-ras (G13A) cDNA

ATGACTGAAT ATAAACTTGT GGTAGTTGGA GCTGGTGXXG TAGGCAAGAG TGCCTTGACG ATACAGCTAA 70
TTCAGAATCA TTTTGTGGAC GAATATGATC CAACAATAGA GGATTCCTAC AGGAAGCAAG TAGTAATTGA 140
TGGAGAAACC TGTCTCTTGG ATATTCTCGA CACAGCAGGT CAAGAGGAGT ACAGTGCAAT GAGGGACCAG 210
TACATGAGGA CTGGGGAGGG CTTTCTTTGT GTATTGCCA TAAATAATAC TAAATCATTT GAAGATATTC 280
ACCATTATAG AGAACAAATT AAAAGAGTTA AGGACTCTGA AGATGTACCT ATGGTCCTAG TAGGAAATAA 350
ATGTGATTTG CCTTCTAGAA CAGTAGACAC AAAACAGGCT CAGGACTTAG TGGAATTCCT 420
TTTATTGAAA CATCAGCAAA GACAAGACAG GGTGTTGATG ATGCCTTCTA TACATTAGTT CGAGAAATTC 490
GAAAACATAA AGAAAAGATG AGCAAAGATG GTAAAAGAAG GAAAAAGAAG TCAAAGACAA AGTGTGTAAT 560
TATGTAA 567

(SEQ ID NO: 14) K-ras (G13A) amino acid sequence

MTEYKLVVVG AGAVGKSALT IQLIQNHFVD EYDPTIEDSY RKQVVIDGET 50
CLLDILDTAG QEEYSAMRDQ YMRTGEGFLC VFAINNTKSF EDIHHYREQI 100
KRVKDSEDVP MVLVGNKCDL PSRTVDTKQA QDLARSYGIP FIETSAKTRQ 150
GVDDAFYTLV REIRKHKEKM SKDGKKKKKK SKTKCVIM 188

FIGURE 1H (SEQ ID NO: 15) K-ras (G13D) cDNA

ATGACTGAAT ATAAACTTGT GGTAGTTGGA GCTGGTGACG TAGGCAAGAG TGCCTTGACG ATACAGCTAA 70
TTCAGAATCA TTTTGTGGAC GAATATGATC CAACAATAGA GGATTCCTAC AGGAAGCAAG TAGTAATTGA 140
TGGAGAAACC TGTCTCTTGG ATATTCTCGA CACAGCAGGT CAAGAGGAGT ACAGTGCAAT GAGGGACCAG 210
TACATGAGGA CTGGGGAGGG CTTTCTTTGT GTATTGCCA TAAATAATAC TAAATCATTT GAAGATATTC 280
ACCATTATAG AGAACAAATT AAAAGAGTTA AGGACTCTGA AGATGTACCT ATGGTCCTAG TAGGAAATAA 350
ATGTGATTTG CCTTCTAGAA CAGTAGACAC AAAACAGGCT CAGGACTTAG CAAGAAGTTA TGGAATTCCT 420
TTTATTGAAA CATCAGCAAA GACAAGACAG GGTGTTGATG ATGCCTTCTA TACATTAGTT CGAGAAATTC 490
GAAAACATAA AGAAAAGATG AGCAAAGATG GTAAAAAGAA GAAAAAGAAG TCAAAGACAA AGTGTGTAAT 560
TATGTAA 567

(SEQ ID NO: 16) K-ras (G13D) amino acid sequence

MTEYKLVVVG AGDVGKSALT IQLIQNHFVD EYDPTIEDSY RKQVVIDGET 50
CLLDILDTAG QEEYSAMRDQ YMRTGEGFLC VFAINNTKSF EDIHHYREQI 100
KRVKDSEDVP MVLVGNKCDL PSRTVDTKQA QDLARSYGIP FIETSAKTRQ 150
GVDDAFYTLV REIRKHKEKM SKDGKKKKKK SKTKCVIM 188

FIGURE 1I (SEQ ID NO: 17) K-ras (T20M) cDNA

```
ATGACTGAAT ATAAACTTGT GGTAGTTGGA GCTGGTGGCG TAGGCAAGAG TGCCTTG&%G ATACAGCTAA  70
TTCAGAATCA TTTGTGGAC GAATATGATC CAACAATAGA GGATTCCTAC AGGAAGCAAG TAGTAATTGA  140
TGGAGAAACC TGTCTCTTGG ATATTCTCGA CACAGCAGGT CAAGAGGAGT ACAGTGCAAT GAGGGACCAG  210
TACATGAGGA CTGGGGAGGG CTTTCTTTGT GTATTGCCA TAAATAATAC TAAATCATTT GAAGATATTC  280
ACCATTATAG AGAACAAATT AAAAGAGTTA AGGACTCTGA AGATGTACCT ATGGTCCTAG TAGGAAATAA  350
ATGTGATTTG CCTTCTAGAA CAGTAGACAC AAAACAGGCT CAGGACTTAG CAAGAAGTTA TGGAATTCCT  420
TTTATTGAAA CATCAGCAAA GACAAGACAG GGTGTTGATG ATGCCTTCTA TACATTAGTT CGAGAAATTC  490
GAAAACATAA AGAAAAGATG AGCAAAGATG GTAAAAAGAA GAAAAAGAAG TCAAAGACAA AGTGTGTAAT  560
TATGTAA 567
```

(SEQ ID NO: 18) K-ras (T20M) amino acid sequence

```
MTEYKLVVVG AGGVGKSAL% IQLIQNHFVD EYDPTIEDSY RKQVIDGET   50
CLLDILDTAG QEEYSAMRDQ YMRTGEGFLC VFAINNTKSF EDIHHYREQI  100
KRVKDSEDVP MVLVGNKCDL PSRTVDTKQA QDLARSYGIP FIETSAKTRQ  150
GVDDAFYTLV REIRKHKEKM SKDGKKKKKK SKTKCVIM 188
```

K-RAS MUTATIONS AND ANTI-EGFR ANTIBODY THERAPY

This application is a continuation of U.S. patent application Ser. No. 12/046,319, filed Mar. 11, 2008, which claims the benefit of U.S. Provisional Application No. 60/906,943, filed Mar. 13, 2007, both of which are incorporated by reference herein for any purpose.

SEQUENCE LISTING

The instant application contains a Sequence Listing which has been submitted in ASCII format via EFS-Web and is hereby incorporated by reference in its entirety. Said ASCII copy, created on Jun. 12, 2012, is named 118_01_seq_list.txt and is 24,576 bytes in size.

FIELD

The present application relates to K-ras mutations, to polynucleotides encoding mutant K-ras polypeptides, and to methods of identifying K-ras mutations. The present application also relates to methods of diagnosing cancer; and methods and kits for predicting the usefulness of anti-EGFr specific binding agents in the treatment of tumors.

BACKGROUND

Certain applications of monoclonal antibodies in cancer therapy rely on the ability of the antibody to specifically deliver to the cancerous tissues cytotoxic effector functions such as immune-enhancing isotypes, toxins or drugs. An alternative approach is to utilize monoclonal antibodies to directly affect the survival of tumor cells by depriving them of essential extracellular proliferation signals, such as those mediated by growth factors through their cell receptors. One of the attractive targets in this approach is the epidermal growth factor receptor (EGFr), which binds EGF and transforming growth factor α (TGFα) (see, e.g., Ullrich et al., Cell 61:203-212, 1990; Baselga et al., Pharmacol. Ther. 64: 127-154, 1994; Mendelsohn et al., in Biologic Therapy of Cancer 607-623, Philadelphia: J.B. Lippincott Co., 1995; Fan et al., Curr. Opin. Oncol. 10: 67-73, 1998). Binding of EGF or TGFα to EGFr, a 170 kDa transmembrane cell surface glycoprotein, triggers a cascade of cellular biochemical events, including EGFr autophosphorylation and internalization, which culminates in cell proliferation (see, e.g., Ullrich et al., Cell 61:203-212, 1990).

Several observations implicate EGFr in supporting development and progression of human solid tumors. EGFr has been demonstrated to be overexpressed on many types of human solid tumors (see, e.g., Mendelsohn Cancer Cells 7:359 (1989), Mendelsohn Cancer Biology 1:339-344 (1990), Modjtahedi and Dean Int'l J. Oncology 4:277-296 (1994)). For example, EGF-r overexpression has been observed in certain lung, breast, colon, gastric, brain, bladder, head and neck, ovarian, and prostate carcinomas (see, e.g., Modjtahedi and Dean Int'l J. Oncology 4:277-296 (1994)). The increase in receptor levels has been reported to be associated with a poor clinical prognosis (see, e.g., Baselga et al. Pharmacol. Ther. 64: 127-154, 1994; Mendelsohn et al., Biologic Therapy of Cancer pp. 607-623, Philadelphia: J.B. Lippincott Co., 1995; Modjtahedi et al., Int'l. J. of Oncology 4:277-296, 1994; Gullick, Br. Medical Bulletin, 47:87-98, 1991; Salomon et al., Crit. Rev. Oncol. Hematol. 19: 183-232, 1995). Both epidermal growth factor (EGF) and transforming growth factor-alpha (TGF-α) have been demonstrated to bind to EGF-r and to lead to cellular proliferation and tumor growth. In many cases, increased surface EGFr expression was accompanied by production of TGFα or EGF by tumor cells, suggesting the involvement of an autocrine growth control in the progression of those tumors (see, e.g., Baselga et al. Pharmacol. Ther. 64: 127-154, 1994; Mendelsohn et al., Biologic Therapy of Cancer pp. 607-623, Philadelphia: J.B. Lippincott Co., 1995; Modjtahedi et al., Int'l. J. of Oncology 4:277-296, 1994; Salomon et al., Crit. Rev. Oncol. Hematol. 19: 183-232, 1995).

Thus, certain groups have proposed that antibodies against EGF, TGF-α, and EGF-r may be useful in the therapy of tumors expressing or overexpressing EGF-r (see, e.g., Mendelsohn Cancer Cells 7:359 (1989), Mendelsohn Cancer Biology 1:339-344 (1990), Modjtahedi and Dean Int'l J. Oncology 4:277-296 (1994), Tosi et al. Int'l J. Cancer 62:643-650 (1995)). Indeed, it has been demonstrated that anti-EGF-r antibodies blocking EGF and TGF-α binding to the receptor appear to inhibit tumor cell proliferation. At the same time, however, anti-EGF-r antibodies have not appeared to inhibit EGF and TGF-α independent cell growth (Modjtahedi and Dean Int'l J. Oncology 4:277-296 (1994)).

Monoclonal antibodies specific to the human EGFr, capable of neutralizing EGF and TGFα binding to tumor cells and of inhibiting ligand-mediated cell proliferation in vitro, have been generated from mice and rats (see, e.g., Baselga et al., Pharmacol. Ther. 64: 127-154, 1994; Mendelsohn et al., in Biologic Therapy of Cancer pp. 607-623, Philadelphia: J.B. Lippincott Co., 1995; Fan et al., Curr. Opin. Oncol. 10: 67-73, 1998; Modjtahedi et al., Int'l. J. Oncology 4: 277-296, 1994). Some of those antibodies, such as the mouse 108, 225 (see, e.g., Aboud-Pirak et al., J. Natl. Cancer Inst. 80: 1605-1611, 1988) and 528 (see, e.g., Baselga et al., Pharmacol. Ther. 64: 127-154, 1994; Mendelsohn et al., in Biologic Therapy of Cancer pp. 607-623, Philadelphia: J.B. Lippincott Co., 1995) or the rat ICR16, ICR62 and ICR64 (see, e.g., Modjtajedi et al., Int'l. J. Oncology 4: 277-296, 1994; Modjtahedi et al., Br. J. Cancer 67:247-253, 1993; Modjtahedi et al., Br. J. Cancer 67: 254-261, 1993) monoclonal antibodies, were evaluated extensively for their ability to affect tumor growth in xenograft mouse models. Most of the anti-EGFr monoclonal antibodies were efficacious in preventing tumor formation in athymic mice when administered together with the human tumor cells (Baselga et al. Pharmacol. Ther. 64: 127-154, 1994; Modjtahedi et al., Br. J. Cancer 67: 254-261, 1993). When injected into mice bearing established human tumor xenografts, the mouse monoclonal antibodies 225 and 528 caused partial tumor regression and required the co-administration of chemotherapeutic agents, such as doxorubicin or cisplatin, for eradication of the tumors (Baselga et al. Pharmacol. Ther. 64: 127-154, 1994; Mendelsohn et al., in Biologic Therapy of Cancer pp. 607-623, Philadelphia: J.B. Lippincott Co., 1995; Fan et al., Cancer Res. 53: 4637-4642, 1993; Baselga et al., J. Natl. Cancer Inst. 85: 1327-1333, 1993). A chimeric version of the 225 monoclonal antibody (C225), in which the mouse antibody variable regions are linked to human constant regions, exhibited an improved in vivo anti-tumor activity but only at high doses (see, e.g., Goldstein et al., Clinical Cancer Res. 1: 1311-1318, 1995; Prewett et al., J. Immunother. Emphasis Tumor Immunol. 19: 419-427, 1996). The rat ICR16, ICR62, and ICR64 antibodies caused regression of established tumors but not their complete eradication (Modjtahedi et al., Br. J. Cancer 67: 254-261, 1993). These results established EGFr as a promising target for antibody therapy against EGFr-expressing solid tumors and led to human clinical trials with the C225 monoclonal antibody in multiple human solid cancers (see, e.g., Baselga et al. *Pharmacol. Ther.* 64: 127-154, 1994; Mendelsohn et al., *Biologic Therapy of Cancer pp.* 607-623, Philadelphia: J.B. Lippincott Co., 1995; Modjtahedi et al., *Int'l. J. of Oncology* 4:277-296, 1994).

Certain advances in the biological arts made it possible to produce a fully human anti-EGFr antibody. Using mice transgenic for human immunoglobulin genes (Xenomouse™ technology, Abgenix, Inc.), human antibodies specific for human EGFr were developed (see, e.g., Mendez, *Nature Genetics*, 15: 146-156, 1997; Jakobovits, *Adv. Drug Deliv. Rev.*, 31(1-2): 33-42, 1998; Jakobovits, *Expert Opin. Invest. Drugs*, 7(4): 607-614, 1998; Yang et al., *Crit. Rev. Oncol. Hematol.* 38(1):17-23, 2001; WO98/24893; WO 98/50433). One such antibody, panitumumab, a human IgG2 monoclonal antibody with an affinity of $5\times10^{-11}$ M for human EGFr, has been shown to block binding of EGF to the EGFr, to block receptor signaling, and to inhibit tumor cell activation and proliferation in vitro (see, e.g., WO98/50433; U.S. Pat. No. 6,235,883). Studies in athymic mice have demonstrated that panitumumab also has in vivo activity, not only preventing the formation of human epidermoid carcinoma A431 xenografts in athymic mice, but also eradicating already-established large A431 tumor xenografts (see, e.g., Yang et al., *Crit. Rev. Oncol. Hematol.* 38(1):17-23, 2001; Yang et al., *Cancer Res.* 59(6):1236-43, 1999). Panitumumab has been considered for the treatment of renal carcinoma, colorectal adenocarcinoma, prostate cancer, and non small cell squamous lung carcinoma, among other cancers (see, e.g., U.S. Patent Publication No. 2004/0033543), and clinical trials are underway with that antibody. Panitumumab has been approved by the Food & Drug Administration to treat patients with metastatic colorectal cancer.

Activation of EGFr triggers at least two signalling pathways. In certain cell types, activation of EGFr prevents apoptosis by stimulation of phosphatidylinositol 3-kinase ("PI3K"). PI3K activation triggers a molecular cascade leading to the downregulation of the central pathways controlling programmed cell death (Yao, R., *Science* 267:2003-2006, 1995). In certain cell types, activation of EGFr initiates the MAPK cascade through Ras/Raf.

SUMMARY

In certain embodiments, a method of predicting whether a patient will be nonresponsive to treatment with a specific binding agent to an EGFr polypeptide is provided. In certain embodiments, the method comprises determining the presence or absence of a K-ras mutation in a tumor of the patient, wherein the K-ras mutation is in codon 12 or codon 13 or codon 20. In certain embodiments, if a K-ras mutation is present, the patient is predicted to be nonresponsive to treatment with a specific binding agent to an EGFr polypeptide.

In certain embodiments, a method of predicting whether a tumor will be nonresponsive to treatment with a specific binding agent to an EGFr polypeptide is provided. In certain embodiments, the method comprises determining the presence or absence of a K-ras mutation in a sample of said tumor, wherein the K-ras mutation is in codon 12 or codon 13 or codon 20. In certain embodiments, the presence of the K-ras mutation indicates that the tumor will be nonresponsive to treatment with a specific binding agent to an EGFr polypeptide.

BRIEF DESCRIPTION OF THE FIGURES

FIGS. 1A to 1I show the cDNA and amino acid sequences for wild-type K-ras (SEQ ID NOs: 1 and 2), G12S mutant K-ras (SEQ ID NOs: 3 and 4), G12V mutant K-ras (SEQ ID NOs: 5 and 6), G12D mutant K-ras (SEQ ID NOs: 7 and 8), G12A mutant K-ras (SEQ ID NOs: 9 and 10), G12C mutant K-ras (SEQ ID NOs: 11 and 12), G13A mutant K-ras (SEQ ID NOs: 13 and 14), G13D mutant K-ras (SEQ ID NOs: 15 and 16), and T20M mutant K-ras (SEQ ID NOs: 17 and 18).

DETAILED DESCRIPTION OF CERTAIN EMBODIMENTS

All references cited herein, including patents, patent applications, papers, textbooks, and the like, and the references cited therein, to the extent that they are not already, are hereby incorporated herein by reference in their entirety. In the event that one or more of the documents incorporated by reference defines a term that contradicts that term's definition in this application, this application controls. The section headings used herein are for organizational purposes only and are not to be construed as limiting the subject matter described.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to the manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

In this application, the use of "or" means "and/or" unless stated otherwise. In the context of a multiple dependent claim, the use of "or" refers back to more than one preceding independent or dependent claim in the alternative only. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

As utilized in accordance with the present disclosure, the following terms, unless otherwise indicated, shall be understood to have the following meanings:

The terms "isolated polynucleotide" and "isolated nucleic acid" are used interchangeably, and as used herein shall mean a polynucleotide of genomic, cDNA, or synthetic origin or some combination thereof, which by virtue of its origin (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The terms "isolated protein" and "isolated polypeptide" are used interchangeably, and as referred to herein mean a protein of cDNA, recombinant RNA, or synthetic origin, or some combination thereof, which by virtue of its origin, or source of derivation, (1) is not associated with proteins found in nature, (2) is free of other proteins from the same source, e.g. free of murine proteins, (3) is expressed by a cell from a different species, or (4) does not occur in nature.

The terms "polypeptide" and "protein" are used interchangeably and are used herein as a generic term to refer to native protein, fragments, peptides, or analogs of a polypeptide sequence. Hence, native protein, fragments, and analogs are species of the polypeptide genus.

The terminology "X#Y" in the context of a mutation in a polypeptide sequence is art-recognized, where "#" indicates the location of the mutation in terms of the amino acid number of the polypeptide, "X" indicates the amino acid found at that position in the wild-type amino acid sequence, and "Y" indicates the mutant amino acid at that position. For example, the notation "G12S" with reference to the K-ras polypeptide indicates that there is a glycine at amino acid number 12 of the wild-type K-ras sequence, and that glycine is replaced with a serine in the mutant K-ras sequence.

The terms "mutant K-ras polypeptide" and "mutant K-ras protein" are used interchangeably, and refer to a K-ras polypeptide comprising at least one K-ras mutation selected from G12S, G12V, G12D, G12A, G12C, G13A, G13D, and T20M. Certain exemplary mutant K-ras polypeptides include, but are not limited to, allelic variants, splice variants, derivative variants, substitution variants, deletion variants, and/or insertion variants, fusion polypeptides, orthologs, and interspecies homologs. In certain embodiments, a mutant K-ras polypeptide includes additional residues at the C- or N-terminus, such as, but not limited to, leader sequence residues, targeting residues, amino terminal methionine residues, lysine residues, tag residues and/or fusion protein residues.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to the positioning of components such that they are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism; in prokaryotes, such control sequences generally include promoter, ribosomal binding site, and transcription termination sequences; in eukaryotes, generally, such control sequences include promoters and transcription termination sequences. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g. for probes, although oligonucleotides may be double stranded, e.g. for use in the construction of a gene mutant. Oligonucleotides of the invention can be either sense or antisense oligonucleotides.

The terms "mutant K-ras polynucleotide", "mutant K-ras oligonucleotide," and "mutant K-ras nucleic acid" are used interchangeably, and refer to a polynucleotide encoding a K-ras polypeptide comprising at least one K-ras mutation selected from G12S, G12V, G12D, G12A, G12C, G13A, G13D, and T20M.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselenoate, phosphorodiselenoate, phosphoroanilothioate, phoshoraniladate, phosphoroamidate, and the like. See e.g., LaPlanche et al. *Nucl. Acids Res.* 14:9081 (1986); Stec et al. *J. Am. Chem. Soc.* 106:6077 (1984); Stein et al. *Nucl. Acids Res.* 16:3209 (1988); Zon et al. *Anti-Cancer Drug Design* 6:539 (1991); Zon et al. *Oligonucleotides and Analogues: A Practical Approach*, pp. 87-108 (F. Eckstein, Ed., Oxford University Press, Oxford England (1991)); Stec et al. U.S. Pat. No. 5,151,510; Uhlmann and Peyman *Chemical Reviews* 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides, and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between polynucleotides, oligonucleotides, and fragments and a nucleic acid sequence of interest will be at least 80%, and more typically with preferably increasing homologies of at least 85%, 90%, 95%, 96%, 97%, 98%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of more than 5 (in standard deviation units) using the program ALIGN with the mutation data matrix and a gap penalty of 6 or greater. See Dayhoff, M. O., in *Atlas of Protein Sequence and Structure*, pp. 101-110 (Volume 5, National Biomedical Research Foundation (1972)) and Supplement 2 to that volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, or at least 24 nucleotides or 8 amino acids in length, or at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (U.S.A.)* 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 96, 97, 98, or 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. The term "amino acid" or "amino acid residue," as used herein, refers to naturally occurring L amino acids or to D amino acids. The commonly used one- and three-letter abbreviations for amino acids are used herein (Bruce Alberts et al., *Molecular Biology of the Cell*, Garland Publishing, Inc., New York (4th ed. 2002)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction. Sequence regions on the DNA strand having the same sequence as the RNA and which are 5' to the 5' end of the RNA transcript are referred to as "upstream sequences". Sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95, 96, 97, or 98 percent sequence identity, and most preferably at least 99 percent sequence identity. Preferably, residue positions which are not identical differ by conservative amino acid substitutions. As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. Conservative amino acid substitutions are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; phenylalanine, tryptophan, and tyrosine are an aromatic family, and cysteine and methionine as a sulfur-containing side chain family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Preferred conservative amino acid substitution groups are: valine-leucine-isoleucine, phenylalanine-tyrosine, lysine-arginine, alanine-valine, glutamic acid-aspartic acid, cysteine-methionine, and asparagine-glutamine.

Preferred amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in *Proteins, Structures and Molecular Principles* (Creighton, Ed., W.H. Freeman and Company, New York (1984)); *Introduction to Protein Structure* (C. Branden and J. Tooze, eds., Garland Publishing, New York, N.Y. (1991)); and Thornton et al. *Nature* 354:105 (1991), which are each incorporated herein by reference.

The term "analog" as used herein refers to polypeptides which are comprised of a segment of at least 25 amino acids that has substantial identity to a portion of an amino acid sequence of a naturally occurring polypeptide and which has at least one of the activities of the naturally occurring polypeptide. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. Those types of non-peptide compound are termed "peptide mimetics" or "peptidomimetics". Fauchere, *J. Adv. Drug Res.* 15:29 (1986); Veber and Freidinger *TINS* p. 392 (1985); and Evans et al. *J. Med. Chem.* 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH—(cis and trans), —$COCH_2$—, —CH(OH)$CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch *Ann. Rev. Biochem.* 61:387 (1992), incorporated herein by reference); for example, by adding internal cysteine residues capable of forming intramolecular disulfide bridges which cyclize the peptide.

Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (see Bowie et al. *Science* 253:164 (1991)). Those of skill in the art can recognize sequence motifs and structural conformations that may be used to define structural and functional domains in accordance with the invention.

The term "specific binding agent" refers to a natural or non-natural molecule that specifically binds to a target. Examples of specific binding agents include, but are not limited to, proteins, peptides, nucleic acids, carbohydrates, lipids, and small molecule compounds. In certain embodiments, a specific binding agent is an antibody. In certain embodiments, a specific binding agent is an antigen binding region.

The term "specific binding agent to an EGFr polypeptide" refers to a specific binding agent that specifically binds any portion of an EGFr polypeptide. In certain embodiments, a specific binding agent to an EGFr polypeptide is an antibody to an EGFr polypeptide. In certain embodiments, a specific binding agent to an EGFr polypeptide is an antigen binding region. In certain embodiments, a specific binding agent to an EGFr polypeptide is an antibody to EGFr. In certain embodiments, a specific binding agent to an EGFr polypeptide is panitumumab.

The term "specific binding agent to a mutant K-ras polypeptide" refers to a specific binding agent that specifically binds any portion of a mutant K-ras polypeptide. In certain embodiments, a specific binding agent to a mutant K-ras polypeptide is an antibody to a mutant K-ras polypeptide. In certain embodiments, a specific binding agent to a mutant K-ras polypeptide is an antigen binding region.

The term "specifically binds" refers to the ability of a specific binding agent to bind to a target with greater affinity than it binds to a non-target. In certain embodiments, specific binding refers to binding for a target with an affinity that is at least 10, 50, 100, 250, 500, or 1000 times greater than the affinity for a non-target. In certain embodiments, affinity is determined by an affinity ELISA assay. In certain embodiments, affinity is determined by a BIAcore assay. In certain embodiments, affinity is determined by a kinetic method. In certain embodiments, affinity is determined by an equilibrium/solution method. In certain embodiments, an antibody is said to specifically bind an antigen when the dissociation constant between the antibody and one or more of its recognized epitopes is ≤1 µM, preferably ≤100 nM and most preferably ≤10 nM.

"Native antibodies and immunoglobulins", in certain instances, are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al. *J. Mol. Biol.* 186:651 (1985; Novotny and Haber, *Proc. Natl. Acad. Sci. U.S.A.* 82:4592 (1985); Chothia et al., Nature 342:877-883 (1989)).

The term "antibody" refers to both an intact antibody and a antigen binding fragment thereof which competes with the intact antibody for specific binding. "Antigen binding fragment thereof" refers to a portion or fragment of an intact antibody molecule, wherein the fragment retains the antigen-binding function. Binding fragments are produced by recombinant DNA techniques, or by enzymatic or chemical cleavage of intact antibodies such as by cleavage with papain. Binding fragments include Fab, Fab', F(ab')$_2$, Fv, single-chain antibodies ("scFv"), Fd' and Fd fragments. Methods for producing the various fragments from monoclonal antibodies are well known to those skilled in the art (see, e.g., Pluckthun, 1992, Immunol. Rev. 130:151-188). An antibody other than a "bispecific" or "bifunctional" antibody is understood to have each of its binding sites be identical. An antibody substantially inhibits adhesion of a receptor to a counterreceptor when an excess of antibody reduces the quantity of receptor bound to counterreceptor by at least about 20%, 40%, 60%, or 80%, and more usually greater than about 85%, 90%, 95%, 96%, 97%, 98%, or 99% (as measured in an in vitro competitive binding assay).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and terminal or internal amino acid sequencing by use of a spinning cup sequenator, or (2) to homogeneity by SDS-PAGE under reducing or nonreducing conditions using Coomassie blue or, preferably, silver stain. An isolated antibody includes the antibody in situ within recombinant cells since at least one component of the antibody's natural environment will not be present. Ordinarily, however, isolated antibody will be prepared by at least one purification step.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al. (1991). The constant domains are not involved directly in binding an antibody to an antigen, but exhibit various effector functions, such as participation of the antibody in antibody-dependent cellular toxicity.

"Fv" is the minimum antibody fragment which contains a complete antigen-recognition and binding site. In a two-chain Fv species, this region comprises a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity on the antibody. However, even a single variable domain (or half of an Fv comprising only three CDRs specific for an antigen) has the ability to recognize and bind antigen, although at a lower affinity than the entire binding site.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-62 (L2), and 89-97 (L3) in the light chain variable domain and 31-55 (H1), 50-65 (H2) and 95-102 (H3) in the heavy chain variable domain; Kabat et al., *Sequences of Proteins of Immunological Interest*, 5$^{th}$ Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 ((H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

The term "complementarity determining regions" or "CDRs," when used herein, refers to parts of immunological receptors that make contact with a specific ligand and determine its specificity. The CDRs of immunological receptors are the most variable part of the receptor protein, giving receptors their diversity, and are carried on six loops at the distal end of the receptor's variable domains, three loops coming from each of the two variable domains of the receptor.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. Nos. 5,500,362, or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS (USA)* 95:652-656 (1988).

The term "epitope" includes any protein determinant capable of specific binding to an immunoglobulin and/or T-cell receptor. Epitopic determinants usually consist of chemically active surface groupings of molecules such as amino acids or sugar side chains and usually have specific three dimensional structural characteristics, as well as specific charge characteristics.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, β-galactosidase, luciferase, alkaline phosphatase), chemiluminescent groups, biotinyl groups, and predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The term "pharmaceutical agent or drug" as used herein refers to a chemical compound or composition capable of inducing a desired therapeutic effect when properly administered to a patient. Other chemistry terms herein are used according to conventional usage in the art, as exemplified by *The McGraw-Hill Dictionary of Chemical Terms* (Parker, S., Ed., McGraw-Hill, San Francisco (1985)), incorporated herein by reference).

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents. In certain embodiments, an antineoplastic agent is panitumumab.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, 96, 97, 98, or 99%. Most preferably, the object species is purified to essential homogeneity (contaminant species cannot be detected in the composition by conventional detection methods) wherein the composition consists essentially of a single macromolecular species.

The term patient includes human and animal subjects.

The terms "mammal" and "animal" for purposes of treatment refers to any animal classified as a mammal, including humans, domestic and farm animals, and zoo, sports, or pet animals, such as dogs, horses, cats, cows, etc. Preferably, the mammal is human.

The term "disease state" refers to a physiological state of a cell or of a whole mammal in which an interruption, cessation, or disorder of cellular or body functions, systems, or organs has occurred.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "responsive" as used herein means that a patient or tumor shows a complete response or a partial response after administering an agent, according to RECIST (Response Evaluation Criteria in Solid Tumors). The term "nonresponsive" as used herein means that a patient or tumor shows stable disease or progressive disease after administering an agent, according to RECIST. RECIST is described, e.g., in Therasse et al., February 2000, "New Guidelines to Evaluate the Response to Treatment in Solid Tumors," J. Natl. Cancer Inst. 92(3): 205-216, which is incorporated by reference herein in its entirety. Exemplary agents include specific binding agents to an EGFr polypeptide, including but not limited to, antibodies to EGFr.

A "disorder" is any condition that would benefit from one or more treatments. This includes chronic and acute disorders or disease including those pathological conditions which predispose the mammal to the disorder in question. Non-limiting examples of disorders to be treated herein include benign and malignant tumors, leukemias, and lymphoid malignancies, in particular breast, rectal, ovarian, stomach, endometrial, salivary gland, kidney, colon, thyroid, pancreatic, prostate or bladder cancer. A preferred disorder to be treated in accordance with the present invention is a malignant tumor, such as cervical carcinomas and cervical intraepithelial squamous and glandular neoplasia, renal cell carcinoma (RCC), esophageal tumors, and carcinoma-derived cell lines.

A "disease or condition related to an EGFr polypeptide" includes one or more of the following: a disease or condition caused by an EGFr polypeptide; a disease or condition contributed to by an EGFr polypeptide; and a disease or condition that is associated with the presence of an EGFr polypeptide. In certain embodiments, a disease or condition related to an EGFr polypeptide is a cancer. Exemplary cancers include, but are not limited to, non small cell lung carcinoma, breast, colon, gastric, brain, bladder, head and neck, ovarian, and prostate carcinomas.

A "disease or condition related to a mutant K-ras polypeptide" includes one or more of the following: a disease or condition caused by a mutant K-ras polypeptide; a disease or condition contributed to by a mutant K-ras polypeptide; a disease or condition that causes a mutant K-ras polypeptide; and a disease or condition that is associated with the presence of a mutant K-ras polypeptide. In certain embodiments, the disease or condition related to a mutant K-ras polypeptide may exist in the absence of the mutant K-ras polypeptide. In certain embodiments, the disease or condition related to a mutant K-ras polypeptide may be exacerbated by the presence of a mutant K-ras polypeptide. In certain embodiments, a disease or condition related to a mutant K-ras polypeptide is a cancer. Exemplary cancers include, but are not limited to, non small cell lung carcinoma, breast, colon, gastric, brain, bladder, head and neck, ovarian, and prostate carcinomas.

In "combined therapy," patients are treated with a specific binding agent for a target antigen in combination with a chemotherapeutic or antineoplastic agent and/or radiation therapy. In certain embodiments, the specific binding agent is panitumumab. Protocol designs will address effectiveness as assessed by reduction in tumor mass as well as the ability to reduce usual doses of standard chemotherapy. These dosage reductions will allow additional and/or prolonged therapy by reducing dose-related toxicity of the chemotherapeutic agent.

"Monotherapy" refers to the treatment of a disorder by administering immunotherapy to patients without an accompanying chemotherapeutic or antineoplastic agent. In certain embodiments, monotherapy comprises administering panitumumab in the absence of a chemotherapeutic or antineoplastic agent and/or radiation therapy.

Certain Embodiments

In certain embodiments, a method of diagnosing a disease or condition which is related to one or more K-ras mutations in a subject is provided.

In certain embodiments, a method of diagnosing a disease or condition which is related to one or more K-ras mutations in a subject comprises: (a) determining the presence or amount of expression of a mutant K-ras polypeptide in a sample from the subject; and (b) diagnosing a disease or condition which is related to one or more K-ras mutations based on the presence or amount of expression of the polypeptide. In certain embodiments, a method of diagnosing a disease or condition which is related to one or more K-ras mutations in a subject comprises: (a) determining the presence or amount of transcription or translation of a mutant K-ras polynucleotide in a sample from the subject; and (b) diagnosing a disease or condition which is related to one or more K-ras mutations based on the presence or amount of transcription or translation of the polynucleotide. In certain embodiments, the disease or condition is cancer.

In certain embodiments, a method of diagnosing a disease or condition which is related to one or more K-ras mutations in a subject comprises: (a) determining the presence or amount of expression of a polypeptide comprising at least one amino acid sequence selected from SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18; and (b) diagnosing a disease or condition which is related to one or more K-ras mutations based on the presence or amount of expression of the polypeptide. In certain embodiments, a method of diagnosing a disease or condition which is related to one or more K-ras mutations in a subject comprises: (a) determining the presence or amount of transcription or translation of a polynucleotide encoding at least one amino acid sequence selected from SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18 in a sample from the subject; and (b) diagnosing a disease or condition which is related to one or more K-ras mutations based on the presence or amount of transcription or translation of the polynucleotide. In certain embodiments, the disease or condition is cancer.

In certain embodiments, a method of diagnosing a susceptibility to a disease or condition which is related to one or more K-ras mutations in a subject is provided. In certain embodiments, a method of diagnosing a susceptibility to a disease or condition which is related to one or more K-ras mutations in a subject comprises: (a) determining the presence or amount of expression of a mutant K-ras polypeptide in a sample from the subject; and (b) diagnosing a susceptibility to a disease or condition which is related to one or more K-ras mutations based on the presence or amount of expression of the polypeptide. In certain embodiments, a method of diagnosing a susceptibility to a disease or condition which is related to one or more K-ras mutations in a subject comprises: (a) determining the presence or amount of transcription or translation of a mutant K-ras polynucleotide in a sample from the subject; and (b) diagnosing a susceptibility to a disease or condition which is related to one or more K-ras mutations based on the presence or amount of transcription or translation of the polynucleotide. In certain embodiments, the disease or condition is cancer.

In certain embodiments, a method of diagnosing a susceptibility to a disease or condition which is related to one or more K-ras mutations in a subject comprises: (a) determining the presence or amount of expression of a polypeptide comprising at least one amino acid sequence selected from SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18 in a sample from the subject; and (b) diagnosing a susceptibility to a disease or condition which is related to one or more K-ras mutations based on the presence or amount of expression of the polypeptide. In certain embodiments, a method of diagnosing a susceptibility to a disease or condition which is related to one or more K-ras mutations in a subject comprises: (a) determining the presence or amount of transcription or translation of a polynucleotide encoding at least one amino acid sequence selected from SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18 in a sample from the subject; and (b) diagnosing a susceptibility to a disease or condition which is related to one or more K-ras mutations based on the presence or amount of transcription or translation of the polypeptide. In certain embodiments, the disease or condition is cancer.

In certain embodiments, a method of determining the presence or absence of a polynucleotide encoding a mutant K-ras polypeptide is provided. In certain embodiments, a method of determining the presence or absence of a polynucleotide encoding a mutant K-ras polypeptide in a sample comprises (a) exposing a sample to a probe which hybridizes to a polynucleotide encoding a region of a mutant K-ras polypeptide, wherein the region comprises at least one K-ras mutation selected from G12S, G12V, G12D, G12A, G12C, G13A, G13D, and T20M, and (b) determining the presence or absence of a polynucleotide encoding a mutant K-ras polypeptide in the sample. In certain embodiments, a method of determining the presence or absence of a mutant K-ras polypeptide in a sample comprises (a) exposing a sample to a probe which hybridizes to a polynucleotide encoding a region of a mutant K-ras polypeptide, wherein the region comprises at least one K-ras mutation selected from G12S, G12V, G12D, G12A, G12C, G13A, G13D, and T20M, and (b) determining the presence or absence of a mutant K-ras polypeptide in the sample.

In certain embodiments, a method for establishing a mutant K-ras population profile in a specific population of individuals is provided comprising: (a) determining the presence of at least one K-ras mutation in a genetic profile of the individuals in a population; and (b) establishing a relationship between mutant K-ras genetic profiles and the individuals. In certain such embodiments, the specific characteristics of the individuals include a susceptibility to developing a disease or condition which is related to a K-ras mutation. In certain such embodiments, the specific characteristics of the individuals include exhibiting a disease or condition which is related to an K-ras mutation.

In certain embodiments, a method of predicting nonresponsiveness to treatment with a specific binding agent to an EGFr polypeptide in a subject suffering from cancer is provided, comprising determining the presence or absence of K-ras mutation G12S in the subject. In certain embodiments, a specific binding agent to an EGFr polypeptide is an antibody to EGFr. In certain such embodiments, the antibody is panitumumab.

In certain embodiments, a method of predicting nonresponsiveness to treatment with a specific binding agent to an EGFr polypeptide in a subject suffering from cancer is provided, comprising determining the presence or absence of K-ras mutation G12V in the subject. In certain embodiments, a specific binding agent to an EGFr polypeptide is an antibody to EGFr. In certain such embodiments, the antibody is panitumumab.

In certain embodiments, a method of predicting nonresponsiveness to treatment with a specific binding agent to an EGFr polypeptide in a subject suffering from cancer is provided, comprising determining the presence or absence of K-ras mutation G12D in the subject. In certain embodiments, a specific binding agent to an EGFr polypeptide is an antibody to EGFr. In certain such embodiments, the antibody is panitumumab.

In certain embodiments, a method of predicting nonresponsiveness to treatment with a specific binding agent to an EGFr polypeptide in a subject suffering from cancer is provided, comprising determining the presence or absence of K-ras mutation G12A in the subject. In certain embodiments, a specific binding agent to an EGFr polypeptide is an antibody to EGFr. In certain such embodiments, the antibody is panitumumab.

In certain embodiments, a method of predicting nonresponsiveness to treatment with a specific binding agent to an EGFr polypeptide in a subject suffering from cancer is provided, comprising determining the presence or absence of K-ras mutation G12O in the subject. In certain embodiments, a specific binding agent to an EGFr polypeptide is an antibody to EGFr. In certain such embodiments, the antibody is panitumumab.

In certain embodiments, a method of predicting nonresponsiveness to treatment with a specific binding agent to an EGFr polypeptide in a subject suffering from cancer is provided, comprising determining the presence or absence of K-ras mutation G13A in the subject. In certain embodiments, a specific binding agent to an EGFr polypeptide is an antibody to EGFr. In certain such embodiments, the antibody is panitumumab.

In certain embodiments, a method of predicting nonresponsiveness to treatment with a specific binding agent to an EGFr polypeptide in a subject suffering from cancer is provided, comprising determining the presence or absence of K-ras mutation G13D in the subject. In certain embodiments, a specific binding agent to an EGFr polypeptide is an antibody to EGFr. In certain such embodiments, the antibody is panitumumab.

In certain embodiments, a method of predicting nonresponsiveness to treatment with a specific binding agent to an EGFr polypeptide in a subject suffering from cancer is provided, comprising determining the presence or absence of K-ras mutation T20M in the subject. In certain embodiments, a specific binding agent to an EGFr polypeptide is an antibody to EGFr. In certain such embodiments, the antibody is panitumumab.

In certain embodiments, a method of predicting nonresponsiveness to treatment with a specific binding agent to an EGFr polypeptide in a subject suffering from cancer is provided, comprising determining the presence or absence of a K-ras mutation at amino acid 12 of K-ras and/or amino acid 13 and/or amino acid 20 of K-ras in the subject. In certain embodiments, a specific binding agent to an EGFr polypeptide is an antibody to EGFr. In certain such embodiments, the antibody is panitumumab.

In certain embodiments, a kit for detecting a polynucleotide encoding a mutant K-ras polypeptide in a subject is provided. In certain such embodiments, the kit comprises a probe which hybridizes to a polynucleotide encoding a region of a mutant K-ras polypeptide, wherein the region comprises at least one K-ras mutation selected from G12S, G12V, G12D, G12A, G12C, G13A, G13D, and T20M. In certain embodiments, the kit further comprises two or more amplification primers. In certain embodiments, the kit further comprises a detection component. In certain embodiments, the kit further comprises a nucleic acid sampling component.

In certain embodiments, nonresponsiveness to treatment with a specific binding agent to an EGFr polypeptide is determined using RECIST (Response Evaluation Criteria in Solid Tumors). Complete response and partial response according to RECIST are both considered to be responsive to treatment with a specific binding agent to an EGFr polypeptide. Stable disease and progressive disease are both considered to be nonresponsive to treatment with a specific binding agent to an EGFr polypeptide. RECIST is known in the art and it described, e.g., in Therasse et al., February 2000, "New Guidelines to Evaluate the Response to Treatment in Solid Tumors," J. Natl. Cancer Inst. 92(3): 205-216, which is incorporated by reference herein for any purpose.

In certain embodiments, a K-ras mutation is detected. In certain embodiments, a K-ras mutation is detected by detecting the mutant K-ras polynucleotide. In certain embodiments, a K-ras mutation is detected by detecting the mutant K-ras polypeptide.

Certain methods of detecting a mutation in a polynucleotide are known in the art. Certain exemplary such methods include, but are not limited to, sequencing, primer extension reactions, electrophoresis, picogreen assays, oligonucleotide ligation assays, hybridization assays, TaqMan assays, SNPlex assays, and assays described, e.g., in U.S. Pat. Nos. 5,470,705, 5,514,543, 5,580,732, 5,624,800, 5,807,682, 6,759,202, 6,756,204, 6,734,296, 6,395,486, and U.S. Patent Publication No. US 2003-0190646 A1.

In certain embodiments, detecting a mutation in a polynucleotide comprises first amplifying a polynucleotide that may comprise the mutation. Certain methods for amplifying a polynucleotide are known in the art. Such amplification products may be used in any of the methods described herein, or known in the art, for detecting a mutation in a polynucleotide.

Certain methods of detecting a mutation in a polypeptide are known in the art. Certain exemplary such methods include, but are not limited to, detecting using a specific binding agent specific for the mutant polypeptide. Other methods of detecting a mutant polypeptide include, but are not limited to, electrophoresis and peptide sequencing.

Certain exemplary methods of detecting a mutation in a polynucleotide and/or a polypeptide are described, e.g., in Schimanski et al. (1999) Cancer Res., 59: 5169-5175; Nagasaka et al. (2004) J. Clin. Oncol., 22: 4584-4596; PCT Publication No. WO 2007/001868 A1; U.S. Patent Publication No. 2005/0272083 A1; and Lievre et al. (2006) Cancer Res. 66: 3992-3994.

In certain embodiments, microarrays comprising one or more polynucleotides encoding one or more mutant K-ras polypeptides are provided. In certain embodiments, microarrays comprising one or more polynucleotides complementary to one or more polynucleotides encoding one or more mutant K-ras polypeptides are provided.

In certain embodiments, the presence or absence of one or more mutant K-ras polynucleotides in two or more cell or tissue samples is assessed using microarray technology. In certain embodiments, the quantity of one or more mutant K-ras polynucleotides in two or more cell or tissue samples is assessed using microarray technology.

In certain embodiments, the presence or absence of one or more mutant K-ras polypeptides in two or more cell or tissue samples is assessed using microarray technology. In certain such embodiments, mRNA is first extracted from a cell or tissue sample and is subsequently converted to cDNA, which is hybridized to the microarray. In certain such embodiments, the presence or absence of cDNA that is specifically bound to the microarray is indicative of the presence or absence of the mutant K-ras polypeptide. In certain such embodiments, the expression level of the one or more mutant K-ras polypeptides is assessed by quantitating the amount of cDNA that is specifically bound to the microarray.

In certain embodiments, microarrays comprising one or more specific binding agents to one or more mutant K-ras polypeptides are provided. In certain such embodiments, the presence or absence of one or more mutant K-ras polypeptides in a cell or tissue is assessed. In certain such embodiments, the quantity of one or more mutant K-ras polypeptides in a cell or tissue is assessed.

The following examples, including the experiments conducted and results achieved are provided for illustrative purpose only and are not to be construed as limiting upon the claims.

EXAMPLES

Example 1

Identification of K-Ras Exon2 Mutations in Colorectal Adenocarcinoma Tumor Samples To identify mutations in K-ras exon 2 associated with colorectal adenocarcinoma ("CRC"), the K-ras exon 2 was amplified from thirty-seven CRC patient tumors. Double-blinded tumor samples from thirty-seven patients enrolled in a CRC trial were obtained prior to patient treatment with panitumumab. The study was a multi-center, open label, single-arm clinical trial. Patients were treated with 2.5 mg/kg panitumumab weekly, repeated in an 8 week cycle until disease progression. Tumor assessments were preformed by blinded central radiology review (a panel of at least 2 radiologists) using RECIST criteria and confirmed no less that 4 weeks after the response criteria were first met. Each isolated exon was sequenced to identify any alterations from the wild-type sequences for those exons.

CRC tumor samples from thirty-seven patients were collected. A portion of each tumor sample was stained to identify the amount of EGFr expression of the tumor and rated for staining on a three-point scale (where 3 is the greatest degree of staining). At least 10% of each tumor sample demonstrated a staining level of three. Tumor tissue was separated from adjacent normal tissue, necrotic debris, and stroma by macro dissection of formalin-fixed, paraffin-embedded tissue sections. Trimmed samples were fixed on microscope slides and stored at room temperature.

TABLE 1

CRC Patient Samples

| Histology Number | Patient Number | Clinical Trial Patient Number |
|---|---|---|
| 05H-5699EB | 17040 | 5149 |
| 04H-405CSB | 17043 | 5152 |
| 04H-406DB | 17046 | 5139 |
| 05H-5700NM | 17049 | 5150 |
| 05H-5698RBR | 17052 | 5147 |
| 05H-5692SM | 17055 | 5093 |
| 05H-5783JMY | 17061 | 5143 |
| 04H-413EED | 17066 | 5151 |
| 05H-5694CS | 17069 | 5141 |
| 05H-5689RBA | 17075 | 5072 |
| 05H-5697IAM | 17078 | 5145 |
| 04H-746XC | 18215 | 5101 |
| 04H-747SH | 18230 | 5133 |
| 04H-748JA | 18244 | 5097 |
| 04H-750GR | 18275 | 5115 |
| 04H-752HBM | 18321 | 5105 |
| 04H-753JR | 18333 | 5106 |
| 04H-754BLB | 18347 | 5113 |
| 04H-755JE | 18361 | 5110 |
| 04H-758GDM | 18396 | 5120 |
| 04H-759JH | 18410 | 5123 |
| 04H-760OGM | 18422 | 5124 |
| 04H-762GRK | 18449 | 5131 |
| 04H-763CHK | 18463 | 5129 |
| 04H-765DB | 18491 | 5136 |
| 04H-766LA | 18505 | 5137 |
| 04H-768LGL | 18526 | 5119 |
| 04H-771WRH | 18554 | 5102 |
| 04H-772CEM | 18569 | 5125 |
| 04H-773LOO | 18583 | 5096 |
| 04H-775BM | 18614 | 5107 |
| 04H-776LAP | 18628 | 5108 |
| 04H-780GL | 18688 | 5135 |
| 04H-781JLK | 18702 | 5121 |
| 05H-5686FEC | 23458 | 5030 |
| 05H-5690JFF | 23481 | 5079 |
| 05H-5696REF | 23534 | 5144 |

Genomic DNA was prepared from the sample slides using the Pinpoint Slide DNA Isolation System (Zymo Research, Orange, Calif.) according to the manufacturer's protocol. The final isolated genomic DNA product was dissolved in 500 µL water.

The wild-type K-ras polypeptide sequence is shown in FIG. 1A (SEQ ID NO: 2; Genbank Accession No. NP_004976). The wild-type K-ras cDNA sequence is also shown in FIG. 1A (SEQ ID NO: 1; Genbank Accession No. NM_004985). The genomic wild-type K-ras nucleotide sequence is found at Genbank Accession No. NM_004985. Primer sequences for each exon were designed using the intron sequences 5' and 3' to exon 2 in the wild-type K-ras cDNA sequence (SEQ ID NO: 1). The sequences corresponding to exon 2 of human K-ras were amplified by PCR using specific primers: primer 3401-41 (5'-AAGGTACTG-GTGGAGTATTTG-3' SEQ ID NO. 19) and primer 3401-44 (5'-GTACTCATGAAAATGGTCAGAG-3' SEQ ID NO. 20).

PCR was performed using Taq DNA polymerase (Roche Diagnostics Corp) or equivalent and the following conditions: 5 µL of 10× Taq buffer, 0.5 µL of 24 mM MgCl2, 1 µL genomic DNA (approximately 0.5 ng), 7 µL of 2.5 mM dNTPs, 1 µL Taq polymerase (5U) and 29.5 µL ddH$_2$O were combined and mixed. 6 µL of combined primer stock (10 µM of each) was added to each tube. The cycle protocol was 1 cycle of 4 minutes at 93° C.; 10 seconds at 93° C., 30 seconds at 62° C., 30 seconds at 72° C. for 35 cycles; and 1 cycle of 4 minutes at 72° C. At the end of the reaction the temperature was held at 4° C.

The PCR products for each individual exon were gel-purified. The purified amplified exon sequences were subcloned into a pCR2.1 vector using a TOPO-TA Cloning Kit (Invitrogen Corp) according to the manufacturer's instructions. E. coli colonies containing the vector and insert exon of interest were picked by a Genetix Colony Picker. Those colonies were grown overnight in liquid medium. Plasmid DNA from each overnight bacterial culture was isolated using a QIAGEN 9600, 3000, or 8000 Bio-robot (Qiagen) according to the manufacturer's instructions.

Isolated plasmid DNA containing each exon was sequenced using a BigDye 3.1 Terminator Kit (Applied Biosystems, Inc.) according to the manufacturer's instructions. Sequencing data was collected using a 3700, 3100, or 3730 Genetic Analyzer (Applied Biosystems, Inc.), and analyzed using the SeQuencher program (GeneCodes Corp.). The exon sequences from the patient samples were compared to the wild-type exon sequences.

The mutational analysis of the CRC patient tumor samples, identified 13 patients with a K-ras exon 2 mutation (Table 2). Tumor response was assessed using CT or MRI and statistically analyzed using RECIST (Response Evaluation Criteria in Solid Tumors), which provides guidelines for identifying complete response, partial response, stable disease, or progressive disease based on tumor size (see, e.g., Therasse et al., February 2000, "New Guidelines to Evaluate the Response to Treatment in Solid Tumors," J. Natl. Cancer Inst. 92(3): 205-216).

TABLE 2

CRC Patient Samples Result

| PTS ID | Mutation | Response |
|---|---|---|
| 5149 | WT | PD |
| 5152 | G12S | PD |
| 5139 | G12V | PD |
| 5150 | WT | PD |
| 5147 | WT | PD |
| 5093 | G12D | SD |
| 5143 | G13D | PD |
| 5151 | WT | PD |
| 5141 | G12V | PD |
| 5072 | WT | PD |
| 5145 | WT | SD |
| 5101 | WT | SD |
| 5133 | WT | SD |
| 5097 | WT | PR |
| 5115 | G12A | SD |
| 5105 | WT | PR |
| 5106 | G12D | PD |
| 5113 | G12C | PD |
| 5110 | WT | SD |
| 5120 | WT | PR |
| 5123 | WT | SD |
| 5124 | WT | PD |
| 5131 | WT | PD |
| 5129 | WT | SD |
| 5136 | WT | PD |
| 5137 | G12V | PD |
| 5119 | WT | SD |
| 5102 | G12V | PD |
| 5125 | G12V, T20M | SD |
| 5096 | WT | SD |
| 5107 | G12D | PD |
| 5108 | WT | PD |
| 5135 | WT | SD |
| 5121 | WT | SD |
| 5030 | WT | PR |
| 5079 | WT | SD |
| 5144 | G12D | PD |

PD stands for progressive disease, PR stands for partial response, and SD stands for stable disease.

Of the thirty-seven tumors, 13 had mutations in exon 2 of K-ras (36%) and 24 were wild-type in exon 2 of K-ras (64%). Of the 13 tumors with a mutation in exon 2 of K-ras, none (0%) showed a partial response to panitumumab. In contrast, 4 of the tumors with wild-type exon 2 of K-ras (17%) showed partial response to panitumumab. Similarly, only 3 (23%) of the tumors with a mutation in exon 2 showed stable disease after panitumumab treatment, while 11 (46%) of the tumors with wild-type exon 2 of K-ras showed stable disease. Finally, 10 (77%) of the tumors with a mutation in exon 2 showed progressive disease after panitumumab treatment, while only 9 (37%) of the tumors with wild-type exon 2 of K-ras showed progressive disease.

Those data are summarized in Table 3.

TABLE 3

Summary of CRC patient mutation status and response to panitumumab

|    | mut+     | mut−     |
|----|----------|----------|
| PR | 0 (0%)   | 4 (17%)  |
| SD | 3 (23%)  | 11 (46%) |
| PD | 10 (77%) | 9 (37%)  |

In that analysis, a mutation in K-ras exon 2, especially mutations G12S, G12V, G12D, G12A, G12C, G13A, G13D, and T20M, were correlated with nonresponsiveness to panitumumab therapy.

Other embodiments will be apparent to those skilled in the art from consideration of the specification and practice of the invention disclosed herein. It is intended that the specification and examples be considered as exemplary only.

We claim:

1. A method of treating a patient with metastatic colorectal cancer comprising determining the presence of a K-ras mutation in a tumor of the patient, said K-ras mutation selected from G13A and T20M, by (i) amplifying at least one K-ras nucleic acid from the tumor using a primer pair specific for at least one K-ras mutation selected from G13A and T20M, wherein said primer pair comprises one primer comprising SEQ ID NO: 19 and a second primer comprising SEQ ID NO: 20; and (ii) sequencing the amplified nucleic acid, wherein if neither of the K-ras mutations are present, administering to the patient an effective amount of panitumumab.

2. The method of claim 1, wherein the K-ras mutation is G13A.

3. The method of claim 1, wherein the K-ras mutation is T20M.

* * * * *

SEQUENCE LISTING

```
<160> NUMBER OF SEQ ID NOS: 20

<210> SEQ ID NO 1
<211> LENGTH: 567
<212> TYPE: DNA
<213> ORGANISM: Homo sapiens

<400> SEQUENCE: 1
atgactgaat ataaacttgt ggtagttgga gctggtggcg taggcaagag tgccttgacg     60
atacagctaa ttcagaatca ttttgtggac gaatatgatc caacaataga ggattcctac    120
aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag ggtgttgatg atgccttcta tacattagtt    480
cgagaaattc gaaaacataa agaaaagatg agcaaagatg gtaaaaagaa gaaaaagaag    540
tcaaagacaa agtgtgtaat tatgtaa                                         567

<210> SEQ ID NO 2
<211> LENGTH: 188
<212> TYPE: PRT
<213> ORGANISM: Homo sapiens

<400> SEQUENCE: 2

Met Thr Glu Tyr Lys Leu Val Val Val Gly Ala Gly Gly Val Gly Lys
1               5                  10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95
```

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 3
<211> LENGTH: 567
<212> TYPE: DNA
<213> ORGANISM: Homo sapiens

<400> SEQUENCE: 3
atgactgaat ataaacttgt ggtagttgga gctagtggcg taggcaagag tgccttgacg    60
atacagctaa ttcagaatca ttttgtggac gaatatgatc caacaataga ggattcctac   120
aggaagcaag tagtaattga tggagaaacc tgtctcttgg atattctcga cacagcaggt   180
caagaggagt acagtgcaat gagggaccag tacatgagga ctggggaggg ctttctttgt   240
gtatttgcca taaataatac taaatcattt gaagatattc accattatag agaacaaatt   300
aaaagagtta aggactctga agatgtacct atggtcctag taggaaataa atgtgatttg   360
ccttctagaa cagtagacac aaaacaggct caggacttag caagaagtta tggaattcct   420
tttattgaaa catcagcaaa gacaagacag ggtgttgatg atgccttcta tacattagtt   480
cgagaaattc gaaaacataa agaaaagatg agcaaagatg gtaaaaagaa gaaaaagaag   540
tcaaagacaa agtgtgtaat tatgtaa                                       567

<210> SEQ ID NO 4
<211> LENGTH: 188
<212> TYPE: PRT
<213> ORGANISM: Homo sapiens

<400> SEQUENCE: 4

Met Thr Glu Tyr Lys Leu Val Val Val Gly Ala Ser Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

```
Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 5
<211> LENGTH: 567
<212> TYPE: DNA
<213> ORGANISM: Homo sapiens

<400> SEQUENCE: 5
atgactgaat ataaacttgt ggtagttgga gctgttggcg taggcaagag tgccttgacg      60
atacagctaa ttcagaatca ttttgtggac gaatatgatc caacaataga ggattcctac     120
aggaagcaag tagtaattga tggagaaacc tgtctcttgg atattctcga cacagcaggt     180
caagaggagt acagtgcaat gagggaccag tacatgagga ctggggaggg ctttctttgt     240
gtatttgcca taaataatac taaatcattt gaagatattc accattatag aacaaatt      300 aaaagagtta aggactctga agatgtacct atggtcctag taggaaataa atgtgatttg     360
ccttctagaa cagtagacac aaaacaggct caggactta caagaagtta tggaattcct     420
tttattgaaa catcagcaaa gacaagacag ggtgttgatg atgccttcta tacattagtt     480
cgagaaattc gaaaacataa agaaaagatg agcaaagatg gtaaaaagaa gaaaaagaag     540
tcaaagacaa agtgtgtaat tatgtaa                                         567

<210> SEQ ID NO 6
<211> LENGTH: 188
<212> TYPE: PRT
<213> ORGANISM: Homo sapiens

<400> SEQUENCE: 6

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
```

```
                        165                 170                 175
Lys Lys Lys Lys Ser Lys Thr Lys Cys Val Ile Met
                180                 185

<210> SEQ ID NO 7
<211> LENGTH: 567
<212> TYPE: DNA
<213> ORGANISM: Homo sapiens

<400> SEQUENCE: 7
atgactgaat ataaacttgt ggtagttgga gctgatggcg taggcaagag tgccttgacg      60
atacagctaa ttcagaatca ttttgtggac gaatatgatc caacaataga ggattcctac    120
aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag gtgttgatg atgccttcta tacattagtt    480
cgagaaattc gaaaacataa agaaaagatg agcaaagatg gtaaaagaa gaaaagaag    540 tcaaagacaa agtgtgtaat tatgtaa                                       567

<210> SEQ ID NO 8
<211> LENGTH: 188
<212> TYPE: PRT
<213> ORGANISM: Homo sapiens

<400> SEQUENCE: 8

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 9
```

<211> LENGTH: 567
<212> TYPE: DNA
<213> ORGANISM: Homo sapiens

<400> SEQUENCE: 9

```
atgactgaat ataaacttgt ggtagttgga gctgctggcg taggcaagag tgccttgacg      60
atacagctaa ttcagaatca ttttgtggac gaatatgatc caacaataga ggattcctac    120
aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taataatac taaatcattt gaagatattc accattatag agaacaaatt    300
aaaagagtta aggactctga agatgtacct atggtcctag taggaaataa atgtgatttg    360
ccttctagaa cagtgacac aaaacaggct caggacttag caagaagtta tggaattcct    420
tttattgaaa catcagcaaa gacaagacag ggtgttgatg atgccttcta tacattagtt    480
cgagaaattc gaaaacataa agaaaagatg agcaagatg gtaaaagaa gaaaagaag      540
tcaaagacaa agtgtgtaat tatgtaa                                        567
```

<210> SEQ ID NO 10
<211> LENGTH: 188
<212> TYPE: PRT
<213> ORGANISM: Homo sapiens

<400> SEQUENCE: 10

```
Met Thr Glu Tyr Lys Leu Val Val Val Gly Ala Ala Gly Val Gly Lys
  1               5                  10                  15
Ser Ala Leu Thr Ile Gln Leu Ile Gln Asn His Phe Val Asp Glu Tyr
             20                  25                  30
Asp Pro Thr Ile Glu Asp Ser Tyr Arg Lys Gln Val Val Ile Asp Gly
         35                  40                  45
Glu Thr Cys Leu Leu Asp Ile Leu Asp Thr Ala Gly Gln Glu Glu Tyr
     50                  55                  60
Ser Ala Met Arg Asp Gln Tyr Met Arg Thr Gly Glu Gly Phe Leu Cys
 65                  70                  75                  80
Val Phe Ala Ile Asn Asn Thr Lys Ser Phe Glu Asp Ile His His Tyr
                 85                  90                  95
Arg Glu Gln Ile Lys Arg Val Lys Asp Ser Glu Asp Val Pro Met Val
            100                 105                 110
Leu Val Gly Asn Lys Cys Asp Leu Pro Ser Arg Thr Val Asp Thr Lys
        115                 120                 125
Gln Ala Gln Asp Leu Ala Arg Ser Tyr Gly Ile Pro Phe Ile Glu Thr
    130                 135                 140
Ser Ala Lys Thr Arg Gln Gly Val Asp Asp Ala Phe Tyr Thr Leu Val
145                 150                 155                 160
Arg Glu Ile Arg Lys His Lys Glu Lys Met Ser Lys Asp Gly Lys Lys
                165                 170                 175
Lys Lys Lys Lys Ser Lys Thr Lys Cys Val Ile Met
            180                 185
```

<210> SEQ ID NO 11
<211> LENGTH: 567
<212> TYPE: DNA
<213> ORGANISM: Homo sapiens

<400> SEQUENCE: 11

```
atgactgaat ataaacttgt ggtagttgga gcttgtggcg taggcaagag tgccttgacg      60
```

-continued

```
atacagctaa ttcagaatca ttttgtggac gaatatgatc caacaataga ggattcctac      120
aggaagcaag tagtaattga tggagaaacc tgtctcttgg atattctcga cacagcaggt      180
caagaggagt acagtgcaat gagggaccag tacatgagga ctggggaggg ctttctttgt      240
gtatttgcca taaataatac taaatcattt gaagatattc accattatag agaacaaatt      300
aaaagagtta aggactctga agatgtacct atggtcctag taggaaataa atgtgatttg      360
ccttctagaa cagtagacac aaaacaggct caggacttag caagaagtta tggaattcct      420
tttattgaaa catcagcaaa gacaagacag ggtgttgatg atgccttcta tacattagtt      480
cgagaaattc gaaaacataa agaaaagatg agcaaagatg gtaaaagaa gaaaaagaag      540 tcaaagacaa agtgtgtaat tatgtaa                                         567
```

<210> SEQ ID NO 12
<211> LENGTH: 188
<212> TYPE: PRT
<213> ORGANISM: Homo sapiens

<400> SEQUENCE: 12

```
Met Thr Glu Tyr Lys Leu Val Val Val Gly Ala Cys Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 13
<211> LENGTH: 567
<212> TYPE: DNA
<213> ORGANISM: Homo sapiens

<400> SEQUENCE: 13

```
atgactgaat ataaacttgt ggtagttgga gctggtgccg taggcaagag tgccttgacg      60
atacagctaa ttcagaatca ttttgtggac gaatatgatc caacaataga ggattcctac      120
aggaagcaag tagtaattga tggagaaacc tgtctcttgg atattctcga cacagcaggt      180
caagaggagt acagtgcaat gagggaccag tacatgagga ctggggaggg ctttctttgt      240
```

```
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag ggtgttgatg atgccttcta tacattagtt    480
cgagaaattc gaaaacataa agaaagatg agcaagatg gtaaaagaa gaaaagaag        540 tcaaagacaa agtgtgtaat tatgtaa                                        567

<210> SEQ ID NO 14
<211> LENGTH: 188
<212> TYPE: PRT
<213> ORGANISM: Homo sapiens

<400> SEQUENCE: 14

Met Thr Glu Tyr Lys Leu Val Val Val Gly Ala Gly Ala Val Gly Lys
  1               5                  10                  15

Ser Ala Leu Thr Ile Gln Leu Ile Gln Asn His Phe Val Asp Glu Tyr
             20                  25                  30

Asp Pro Thr Ile Glu Asp Ser Tyr Arg Lys Gln Val Val Ile Asp Gly
         35                  40                  45

Glu Thr Cys Leu Leu Asp Ile Leu Asp Thr Ala Gly Gln Glu Glu Tyr
     50                  55                  60

Ser Ala Met Arg Asp Gln Tyr Met Arg Thr Gly Glu Gly Phe Leu Cys
 65                  70                  75                  80

Val Phe Ala Ile Asn Asn Thr Lys Ser Phe Glu Asp Ile His His Tyr
                 85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 15
<211> LENGTH: 567
<212> TYPE: DNA
<213> ORGANISM: Homo sapiens

<400> SEQUENCE: 15
atgactgaat ataaacttgt ggtagttgga gctggtgacg taggcaagag tgccttgacg     60
atacagctaa ttcagaatca ttttgtggac gaatatgatc caacaataga ggattcctac    120
aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag ggtgttgatg atgccttcta tacattagtt    480
```

```
cgagaaattc gaaacataa agaaaagatg agcaaagatg gtaaaaagaa gaaaaagaag    540
tcaaagacaa agtgtgtaat tatgtaa                                      567
```

<210> SEQ ID NO 16
<211> LENGTH: 188
<212> TYPE: PRT
<213> ORGANISM: Homo sapiens

<400> SEQUENCE: 16

```
Met Thr Glu Tyr Lys Leu Val Val Gly Ala Gly Asp Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 17
<211> LENGTH: 567
<212> TYPE: DNA
<213> ORGANISM: Homo sapiens

<400> SEQUENCE: 17

```
atgactgaat ataaacttgt ggtagttgga gctggtggcg taggcaagag tgccttgatg     60
atacagctaa ttcagaatca ttttgtggac gaatatgatc caacaataga ggattcctac    120
aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag ggtgttgatg atgccttcta tacattagtt    480
cgagaaattc gaaacataa agaaaagatg agcaaagatg gtaaaaagaa gaaaaagaag    540
tcaaagacaa agtgtgtaat tatgtaa                                      567
```

<210> SEQ ID NO 18

```
<211> LENGTH: 188
<212> TYPE: PRT
<213> ORGANISM: Homo sapiens

<400> SEQUENCE: 18

Met Thr Glu Tyr Lys Leu Val Val Val Gly Ala Gly Gly Val Gly Lys
1               5                   10                  15

Ser Ala Leu Met Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 19
<211> LENGTH: 21
<212> TYPE: DNA
<213> ORGANISM: ARTIFICIAL SEQUENCE
<220> FEATURE:
<223> OTHER INFORMATION: PRIMER SEQUENCE

<400> SEQUENCE: 19
aaggtactgg tggagtattt g                                         21

<210> SEQ ID NO 20
<211> LENGTH: 22
<212> TYPE: DNA
<213> ORGANISM: ARTIFICIAL SEQUENCE
<220> FEATURE:
<223> OTHER INFORMATION: PRIMER SEQUENCE

<400> SEQUENCE: 20
gtactcatga aaatggtcag ag                                        22
```